US012638433B2

(12) United States Patent
Inoue et al.

(10) Patent No.: US 12,638,433 B2
(45) Date of Patent: May 26, 2026

(54) FOOD PHYSICAL PROPERTY ASSESSMENT METHOD

(71) Applicant: Meiji Co., Ltd., Tokyo (JP)

(72) Inventors: Motoki Inoue, Tokyo (JP); Wakako Tanaka, Tokyo (JP); Reina Kanda, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 297 days.

(21) Appl. No.: 18/564,320

(22) PCT Filed: May 27, 2022

(86) PCT No.: PCT/JP2022/021845
§ 371 (c)(1),
(2) Date: Nov. 27, 2023

(87) PCT Pub. No.: WO2022/250167
PCT Pub. Date: Dec. 1, 2022

(65) Prior Publication Data
US 2024/0255484 A1 Aug. 1, 2024

(30) Foreign Application Priority Data
May 28, 2021 (JP) ................................. 2021-090500

(51) Int. Cl.
*G01N 3/34* (2006.01)
*G01N 33/02* (2006.01)
(52) U.S. Cl.
CPC ............... *G01N 33/02* (2013.01); *G01N 3/34* (2013.01)
(58) Field of Classification Search
None
See application file for complete search history.

(56) References Cited

U.S. PATENT DOCUMENTS

| | | | |
|---|---|---|---|
| 6,065,330 A | 5/2000 | Freeman et al. | |
| 2010/0223977 A1 | 9/2010 | Debon et al. | |
| 2010/0228504 A1 | 9/2010 | Takahashi et al. | |

FOREIGN PATENT DOCUMENTS

| | | | | | |
|---|---|---|---|---|---|
| CN | 106644798 A | * | 5/2017 | ............... | G01N 3/56 |
| DE | 202020100966 U | * | 2/2020 | ............. | A61C 19/00 |

(Continued)

OTHER PUBLICATIONS

International Search Report (ISR) issued Aug. 16, 2022 in International (PCT) Application No. PCT/JP2022/021845.

(Continued)

*Primary Examiner* — Daniel S Larkin
(74) *Attorney, Agent, or Firm* — Wenderoth, Lind & Ponack, L.L.P.

(57) ABSTRACT

A food physical property evaluation method includes: placing a food to be evaluated on a lower occlusal part of a lower plunger which has a shape to occlude with an upper occlusal part of an upper plunger and faces the upper occlusal part of the upper plunger; causing the upper plunger or the lower plunger to perform a reciprocating linear movement in a linear direction in which the upper plunger and the lower plunger are occluded and separated, causing the upper plunger or the lower plunger to perform a reciprocating rotation movement in a rotation direction with the linear direction as a rotation axis, and adjusting a pressure applied between the upper plunger and the lower plunger; and measuring a physical quantity including a force and a torque applied to the upper plunger or the lower plunger, and evaluating food physical properties based on the physical quantity.

8 Claims, 25 Drawing Sheets

(56)  References Cited

FOREIGN PATENT DOCUMENTS

| | | |
|---|---|---|
| JP | 2000-507354 | 6/2000 |
| JP | 3338397 B | * 10/2002 |
| JP | 2007-232539 | 9/2007 |
| JP | 2009-162731 | 7/2009 |
| JP | 2010-529438 | 8/2010 |
| JP | 2012-139442 | 7/2012 |
| JP | 2018-146311 | 9/2018 |
| WO | 2021/033619 | 2/2021 |

OTHER PUBLICATIONS

Gustavo Luengo et al., "Thin Film Rheology and Tribology of Chocolate", Journal of Food Science, vol. 62, No. 4, pp. 767-772, Jul. 10, 1997, cited in ISR.
Satoko Shiotsubo, "Application of Thermal Analysis to Food (Part 1)", Cookery Science, 24.1: pp. 54-61, 1991, cited in the specification.

* cited by examiner

FOOD PHYSICAL PROPERTY ASSESSMENT METHOD

CROSS-REFERENCE TO RELATED APPLICATIONS

The present application is a PCT National Phase Entry of PCT/JP2022/021845 filed on May 27, 2022, which claims priority under 35 U.S.C. § 119 to Japanese Patent Application No. 2021-090500, the contents of which are incorporated herein by reference in their entirety.

TECHNICAL FIELD

The present invention relates to a food physical property evaluation method.

BACKGROUND ART

Various measurements are performed in order to evaluate a food texture upon eating. Evaluation of the food texture upon eating due to the measurements is expected to be applied to development in a product suitable for a preference or a chewing force of a consumer.

NPL 1 discloses a research report based on thermal analysis for "melt in mouth" of a chocolate. In the research based on the thermal analysis, a melting behavior alone of oil or fat is measured, and a change in food properties due to an emulsifying effect with saliva which occurs in a mouth, or the like is not taken into consideration.

To provide a mastication simulation device that can obtain a scent component and a taste component close to actual mastication by simulating an environment close to an actual oral environment and simulating actual mastication under the environment, and that can further develop a product in consideration of mastication of consumers by modeling a chewing force of a consumer that is considered to be weak in a masticatory force, such as an infant or an elderly person, PTL 1 discloses a mastication simulation device including a container and a pair of simulative mastication teeth facing each other in the container.

To provide a bolus forming device that can be used to evaluate a food texture of a food by modeling human mastication, PTL 2 discloses a bolus forming device including artificial teeth and an artificial tongue provided in an artificial oral cavity.

CITATION LIST

Patent Literature

PTL 1: JP2009-162731A
PTL 2: WO2021/033619

Non Patent Literature

NPL 1: Satoko Shiotsubo, "Application of Thermal Analysis to Food (Part 1)", Cookery Science, 1991, 24.1: 54-61.

SUMMARY OF INVENTION

Technical Problem

However, there are many cases in which an evaluation result of the food texture obtained by the measurement in the related art does not coincide with an evaluation result of the food texture (sensory evaluation) obtained by actual eating.

One factor is that while the perception of food texture during eating involving a continuous change in food properties from the moment the food enters mouth until it is swallowed, the measurement in the related art are conducted using methods that do not take into consideration the changes in the food properties within the oral cavity.

For example, when a chocolate is eaten, the chocolate melts at a body temperature, receives a vertical stress and a shear stress due to contact with a tongue and an oral mucous membrane, and is emulsified by being mixed with saliva at the same time. These events occur continuously from the vicinity of a chocolate surface, and finally the whole is swallowed in a melted and emulsified state. Therefore, in order to evaluate the food texture of the chocolate by measurement, it is considered necessary to take into account the changes in the food properties according to the above-described continuous events.

Therefore, there is a demand for a food physical property evaluation method in which the change in the food properties in the oral cavity can be simulated and a physical quantity corresponding to perception in the oral cavity can be obtained.

Therefore, an object of the invention is to provide a food physical property evaluation method in which a change in food properties in an oral cavity can be simulated and a physical quantity corresponding to perception in the oral cavity can be obtained.

Solution to Problem

A food physical property evaluation method according to the invention includes: placing a food to be evaluated on a lower occlusal part of a lower plunger which has a shape to occlude with an upper occlusal part of an upper plunger and is provided to face the upper occlusal part of the upper plunger; causing at least one of the upper plunger and the lower plunger to perform a reciprocating linear movement in a linear direction in which the upper plunger and the lower plunger are occluded and separated, causing at least one of the upper plunger and the lower plunger to perform a reciprocating rotation movement in a rotation direction with the linear direction as a rotation axis, and adjusting a pressure applied between the upper plunger and the lower plunger by a method other than pneumatics; and measuring a physical quantity including a force and a torque applied to the upper plunger or the lower plunger, and evaluating food physical properties based on the obtained physical quantity.

Advantageous Effects of Invention

According to the food physical property evaluation method in the invention, a change in food properties in an oral cavity can be simulated, a physical quantity corresponding to perception in the oral cavity can be obtained, and food physical properties can be evaluated.

DESCRIPTION OF EMBODIMENTS

Hereinafter, embodiments of the invention will be described below. The embodiments described below are merely an example, and can be appropriately modified within a range obvious to those skilled in the art.

First Embodiment (Configuration of Food Physical Property Evaluation Device)

Figure 1:
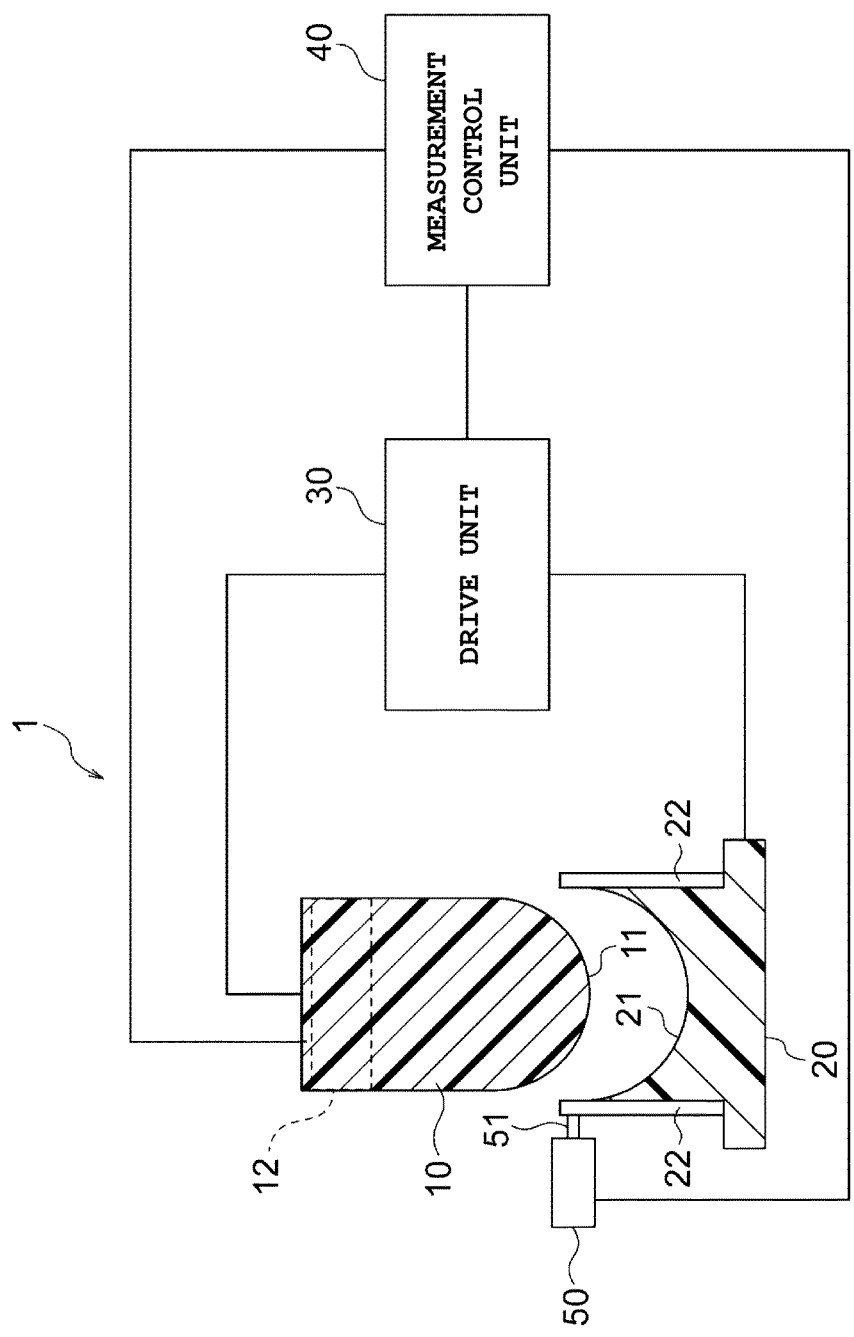
FIG. 1 is a schematic view showing a configuration of a food physical property evaluation device according to a first embodiment.
Figure 2:
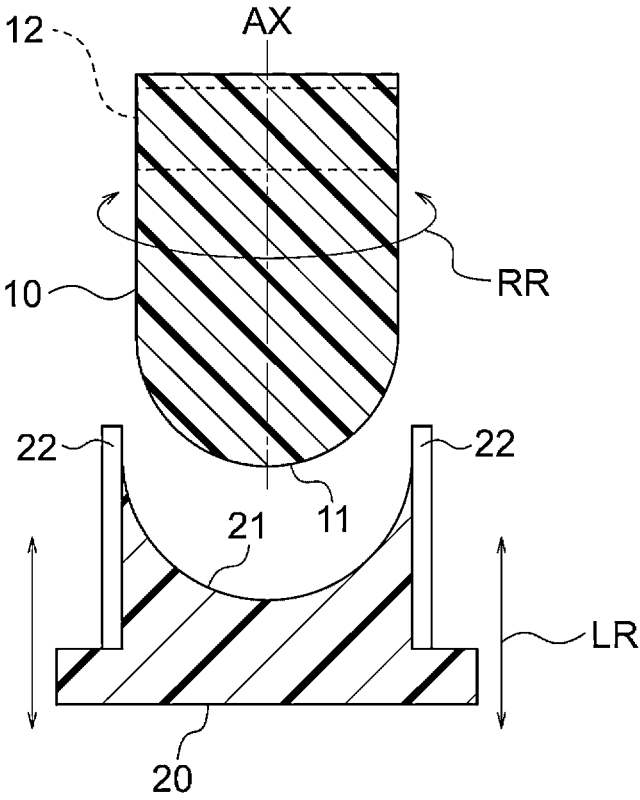
FIG. 2 is a schematic view showing a configuration of an upper plunger and a lower plunger of the food physical property evaluation device in FIG. 1.

FIG. 1 is a schematic view showing a configuration of a food physical property evaluation device 1 according to the embodiment. The food physical property evaluation device 1 includes an upper plunger 10, a lower plunger 20, a sensor 12, a drive unit 30, and a measurement control unit 40. FIG. 2 is a schematic view showing a configuration of the upper plunger 10 and the lower plunger 20 of the food physical property evaluation device 1 in FIG. 1.

The upper plunger 10 and the lower plunger 20 are intraoral models having shapes suitable for evaluation of physical properties of a chocolate, and the food physical property evaluation device 1 according to the embodiment can be suitably used particularly for the evaluation of the physical properties of the chocolate.

The upper plunger 10 is provided with an upper occlusal part 11. The upper occlusal part 11 of the upper plunger 10 has, for example, a hemispherical convex portion at a tip end thereof.

The lower plunger 20 is provided such that a lower occlusal part 21 having a shape to be occluded with the upper occlusal part 11 faces the upper occlusal part 11.

The lower occlusal part 21 has a concave portion to be occluded with the upper occlusal part 11. The concave portion has a shape having a hemispherical surface as an inner wall surface.

The upper plunger 10 and the lower plunger 20 are made of a resin having a hardness suitable for forming the intraoral model, for example, an acrylonitrile-butadiene-styrene copolymer (ABS) resin, an acrylic resin, or a fluorine-containing resin such as polyvinylidene fluoride.

A sensor 12 is incorporated in the upper plunger 10, and measures a physical quantity applied to the upper plunger 10. The sensor 12 may be embedded in the upper plunger 10. The sensor 12 is, for example, a six-axis sensor. The physical quantity measured by the six-axis sensor includes, for example, a force and a torque applied to the upper plunger 10.

The drive unit 30 includes, for example, a motor. The drive unit 30 drives the lower plunger 20 such that the lower plunger 20 performs a reciprocating linear movement LR in a linear direction to occlude with and separated from the upper plunger 10. In addition, the drive unit 30 drives the upper plunger 10 such that the upper plunger 10 performs a reciprocating rotation movement RR in a rotation direction with the linear direction of the reciprocating linear movement LR of the lower plunger 20 as a rotation axis AX.

The food physical property evaluation device 1 includes a pressure adjustment unit that adjusts a pressure applied between the upper plunger 10 and the lower plunger 20 by a method other than pneumatics when the upper occlusal part 11 of the upper plunger 10 and the lower occlusal part 21 of the lower plunger 20 come into contact with each other during occlusion. The pressure adjustment unit includes a motor or a solid elastic body such as a spring, and adjusts the pressure applied between the upper plunger 10 and the lower plunger 20 by power of the motor or an elastic force of the solid elastic body. When the pressure adjustment unit is driven by a motor, the drive unit 30 may be driven by the motor. By using the motor, it is possible to adjust the pressure more easily and with higher accuracy than in the case of using the pneumatics in which hysteresis (a history effect) is large, and it is possible to model a mastication movement.

The measurement control unit 40 controls the reciprocating linear movement LR of the lower plunger 20 and the reciprocating rotation movement RR of the upper plunger 10 by the drive unit 30. The measurement control unit 40 measures the physical quantity applied to the upper plunger 10 based on an output of the sensor 12. The measurement control unit 40 can obtain impulse data by integrating measured force data over time.

The food physical property evaluation device 1 drives the lower plunger 20 to perform the reciprocating linear movement LR by placing a food FA to be evaluated on the lower occlusal part 21, and evaluates physical properties of the food FA based on a physical quantity (a measured value) obtained from the output of the sensor 12 when the upper plunger 10 is driven to perform the reciprocating rotation movement RR.

In the food physical property evaluation device 1, for example, the upper plunger 10 and the lower plunger 20 are disposed at positions where the upper plunger 10 and the lower plunger 20 are not in contact with each other even when the upper plunger 10 and the lower plunger 20 are closest to each other. When the food FA to be evaluated is present on the lower occlusal part 21, a force corresponding to a set compression force is applied from the lower plunger 20 to the food FA, and is further applied to the upper plunger 10 via the food FA. During the occlusion of the upper plunger 10 and the lower plunger 20, a force exceeding the set compression force is not applied.

In the food physical property evaluation device 1, for example, a cylindrical protective part 22 is provided on an outer circumference of the lower plunger 20. The protective part 22 prevents the food FA from jumping out from a space between the upper plunger 10 and the lower plunger 20.

The food physical property evaluation device 1 further includes, for example, an artificial saliva supply unit 50 that adds artificial saliva at a predetermined flow rate and causes the artificial saliva to flow between the upper plunger 10 and the lower plunger 20. An inflow tube 51 extends from the artificial saliva supply unit 50 to the space between the upper plunger 10 and the lower plunger 20 through the protective part 22. Only one inflow tube 51 is provided in FIG. 1, and a plurality of inflow tubes 51 may be provided. Under control of the measurement control unit 40, the artificial saliva is added at the predetermined flow rate and flows between the upper plunger 10 and the lower plunger 20. As the artificial saliva, for example, a 0.02% aqueous solution of xanthan gum whose flow characteristics are approximated to that of saliva can be used. Alternatively, an aqueous solution containing sodium hydrogen carbonate, potassium dihydrogen phosphate trihydrate, sodium chloride, potassium chloride, calcium chloride dihydrate and mucin and adjusted to pH 6.95 with hydrochloric acid can be used. Alternatively, an aqueous solution obtained by adding amylase to these substances may be used.

In the food physical property evaluation device 1, for example, a portion including at least the upper plunger 10 and the lower plunger 20 is adjustable to a predetermined temperature. The predetermined temperature is, for example, a temperature near the body temperature. The portion including the upper plunger 10 and the lower plunger 20 may be the whole food physical property evaluation device 1. The temperature can be adjusted using, for example, a warm air device.

Figure 3:
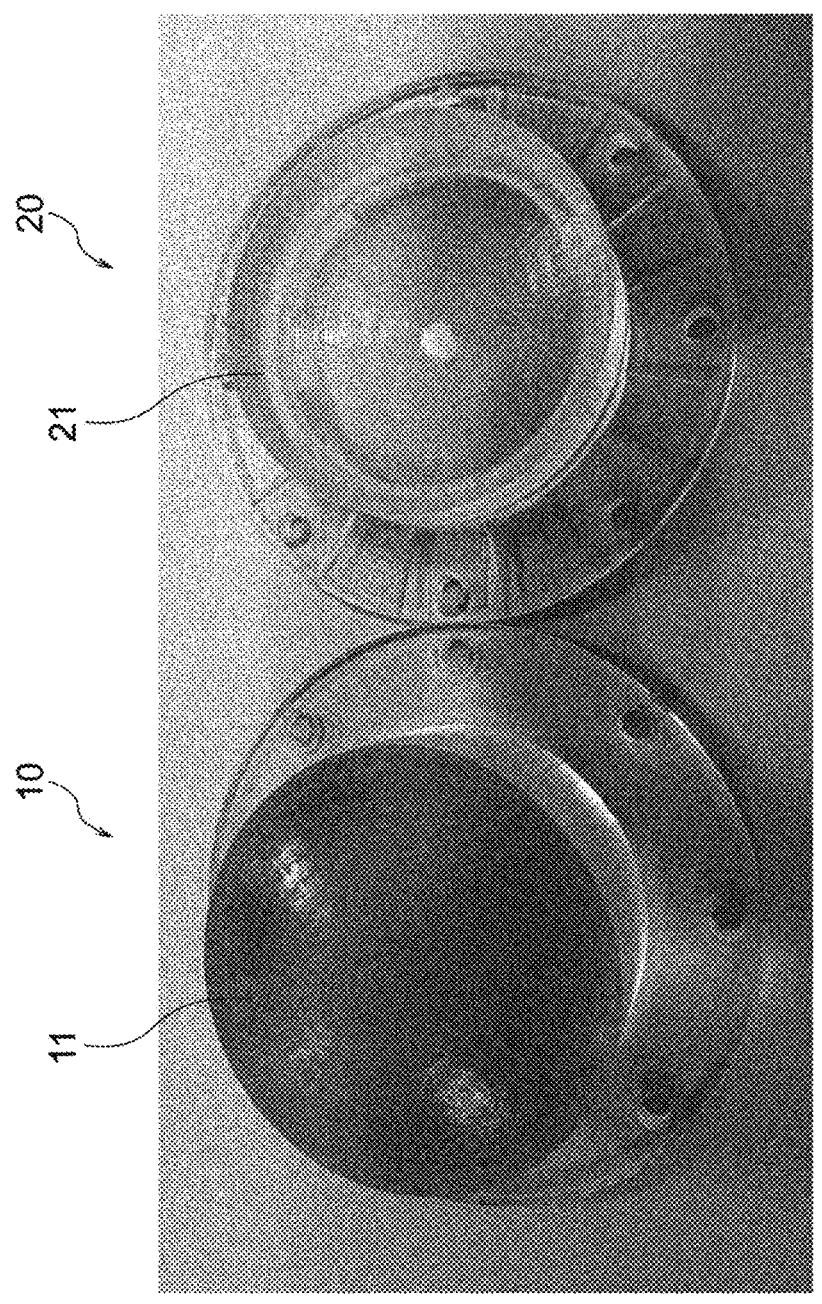
FIG. 3 is a photograph showing an example of the upper plunger and the lower plunger of the food physical property evaluation device in FIG. 1.

FIG. 3 is a photograph showing an example of the upper plunger 10 and the lower plunger 20 of the food physical property evaluation device 1 in FIG. 1. The upper plunger 10 is provided with the upper occlusal part 11 having a hemispherical convex portion at a tip end thereof. The lower plunger 20 is provided with the lower occlusal part 21 having a concave shape having a hemispherical surface as an inner wall surface to occlude with the upper occlusal part 11.

(Food Physical Property Evaluation Method)

A food physical property evaluation method according to the embodiment will be described. The food physical property evaluation method according to the embodiment is performed by using the food physical property evaluation device 1 according to the embodiment. The food physical property evaluation device 1 includes the upper plunger 10 provided with the upper occlusal part 11, the lower plunger 20 provided such that the lower occlusal part 21 having a shape to be occluded with the upper occlusal part 11 faces the upper occlusal part 11, and the sensor 12 that is incorporated in the upper plunger 10 and that measures a physical quantity applied to the upper plunger 10. First, the food FA to be evaluated is placed on the lower occlusal part 21 having such a configuration.

Next, the drive unit 30 drives the lower plunger 20 to perform the reciprocating linear movement LR in a direction in which the lower plunger 20 is to be occluded with the upper plunger 10, and drives the upper plunger 10 such that the upper plunger 10 performs the reciprocating rotation movement RR with a direction of the reciprocating linear movement LR of the lower plunger 20 as the rotation axis AX. When the upper occlusal part 11 of the upper plunger 10 and the lower occlusal part 21 of the lower plunger 20 come into contact with each other during occlusion, the drive unit 30 adjusts the pressure applied between the upper plunger 10 and the lower plunger 20.

Figure 4A:
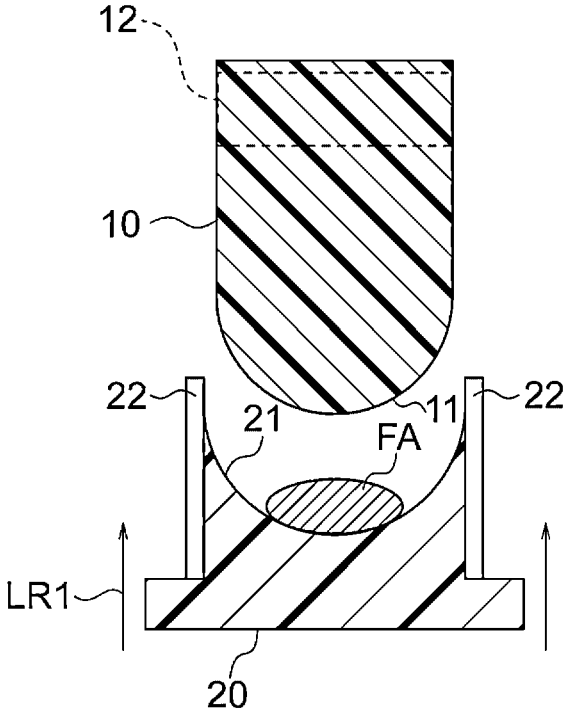
FIG. 4A is a schematic view showing operations of the upper plunger and the lower plunger of the food physical property evaluation device in FIG. 1.

A specific example of operations of the reciprocating linear movement LR of the lower plunger 20 and the reciprocating rotation movement RR of the upper plunger 10 will be described. FIG. 4A is a schematic view showing operations of the upper plunger 10 and the lower plunger 20 of the food physical property evaluation device 1 in FIG. 1. First, the food FA to be evaluated such as a chocolate is placed on the lower occlusal part 21 of the lower plunger 20. Next, the lower plunger 20 is elevated in a first linear movement direction LR1, and the lower occlusal part 21 of the lower plunger 20 occludes with the upper occlusal part 11 of the upper plunger 10.

Figure 4B:
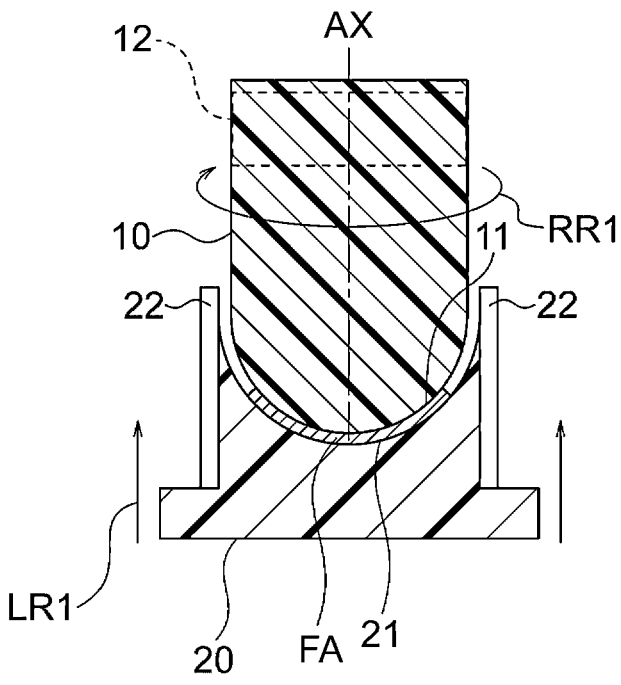
FIG. 4B is a schematic view showing an operation subsequent to FIG. 4A.

Next, as shown in FIG. 4B, when the lower occlusal part 21 of the lower plunger 20 occludes with the upper occlusal part 11 of the upper plunger 10, the food FA is pressed into a gap between the lower occlusal part 21 and the upper occlusal part 11 with a predetermined force. In this state, the upper plunger 10 is rotated in a first rotation movement direction RR1 to cause the upper occlusal part 11 of the upper plunger 10 to slide while being in contact with the food FA.

Figure 4C:
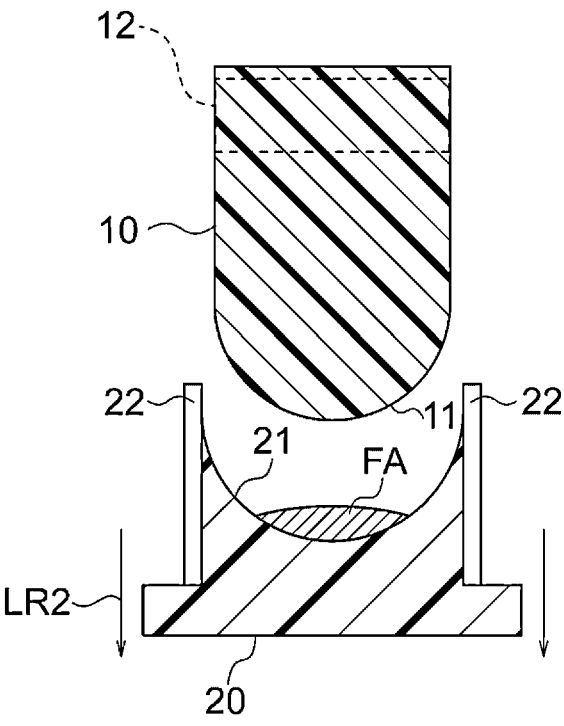
FIG. 4C is a schematic view showing an operation subsequent to FIG. 4B.

Subsequently, as shown in FIG. 4C, rotation of the upper plunger 10 in the first rotation movement direction RR1 is stopped, the lower plunger 20 is lowered in a second linear movement direction LR2, and the occlusion between the lower occlusal part 21 of the lower plunger 20 and the upper occlusal part 11 of the upper plunger 10 is released.

Figure 4D:
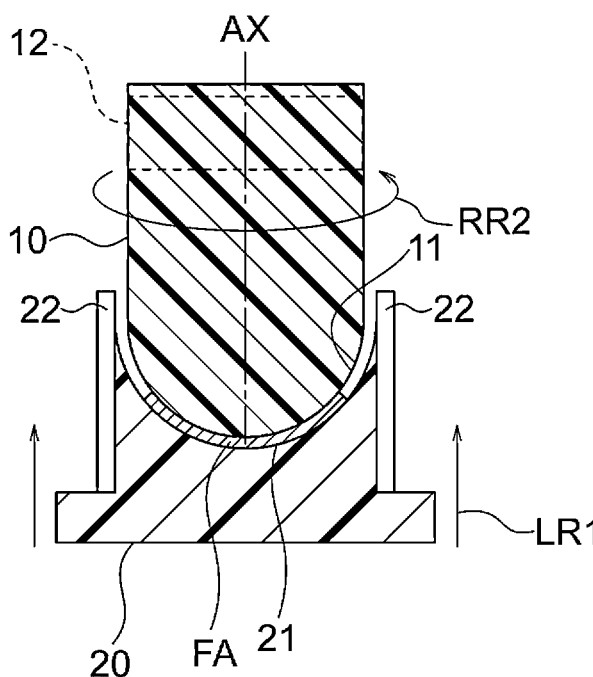
FIG. 4D is a schematic view showing an operation subsequent to FIG. 4C.

Next, as shown in FIG. 4D, the lower plunger 20 is elevated in the first linear movement direction LR1, and the lower occlusal part 21 of the lower plunger 20 occludes with the upper occlusal part 11 of the upper plunger 10. In this state, the upper plunger 10 is rotated in a second rotation movement direction RR2 to cause the upper occlusal part 11 of the upper plunger 10 to slide while being in contact with the food FA.

Thereafter, the operations of FIGS. 4A to 4D are repeatedly performed. Among the operations described above, a step in which the lower plunger 20 is elevated from a lowermost position, occludes with the upper plunger 10, and then lowers again to return to the lowermost position is also referred to as one compression.

As described above, the reciprocating linear movement LR of the lower plunger 20 and the reciprocating rotation movement RR of the upper plunger 10 are performed, and at the same time, the physical quantity is measured based on the output of the sensor 12. The physical properties of the food FA are evaluated based on the obtained physical quantity.

In the food physical property evaluation device 1, items such as a compression force (a maximum force applied to the food), a compression frequency (a number of occlusion per unit time: an occlusion frequency), an artificial saliva addition flow rate, a number of compression (an number of occlusion), and a temperature can be set.

In the food physical property evaluation device 1, an appearance of a bolus during compression and after a predetermined number of times of compression can be visually checked, and the bolus can also be subjected to another physical property measurement. In addition, based on the output of the sensor 12, a force acting on the upper plunger 10 during occlusion and a torque acting on the upper plunger 10 due to rotational sliding between the upper plunger 10 and the lower plunger 20 are measured. The measurement control unit 40 integrates the measured force data over time to obtain the impulse data. In addition, a temporal change in the physical quantity, for example, a temporal change in a force (an impulse obtained when integrated), and a temporal change in a torque are obtained. (Functions and Effects)

The operations of the upper plunger 10 and the lower plunger 20 of the food physical property evaluation device 1 according to the embodiment described above simulate a sliding behavior of a tongue in an oral cavity. According to the food physical property evaluation device 1 in the embodiment, it is possible to simulate the sliding behavior of the tongue to reproduce the change in the food properties in the oral cavity, and to obtain a physical quantity corresponding to perception in the oral cavity. For example, a force (an impulse obtained when integrated) and a torque are obtained for the food to be evaluated. In addition, it is possible to obtain the temporal change in the physical quantity corresponding to the perception in the oral cavity with respect to the food to be evaluated. For example, a temporal change in the force (the impulse obtained when integrated) and a temporal change in the torque are obtained with respect to the food to be evaluated. The food physical properties can be evaluated based on these pieces of data.

In the related art, an intraoral model that simulates the sliding behavior of the tongue is not known. In the food physical property evaluation device 1 according to the embodiment, by simulating the sliding behavior of the tongue, reproducibility of the change in the food properties in the oral cavity can be enhanced, and the physical quantity corresponding to the perception in the oral cavity can be obtained.

In particular, in the food physical property evaluation device 1 according to the embodiment, by measuring the torque applied to the upper plunger 10 or the lower plunger 20, it is possible to obtain the physical quantity corresponding to a feeling of the sliding behavior of the tongue. In addition, in the food physical property evaluation device 1 according to the embodiment, since the reciprocating linear movement is performed in a vertical direction, an actual movement in the oral cavity can be more accurately modeled.

First Example

In the food physical property evaluation device 1 according to the first embodiment, about 2.5 g of a commercially available chocolate sample was used, and a test was conducted in which the upper plunger 10 and the lower plunger 20 were driven in the operations shown in FIGS. 4A to 4D. The treatment was performed for 120 seconds (the number of compression is 120 times) under conditions of a compression interval of 1 time/second, a compression force of 200 N, and an angular velocity of 180°/s (reversing the rotation direction at each compression interval). A temperature of a plunger surface in contact with the chocolate was adjusted to 36.5° C. to 37.0° C. In order to simulate saliva retained in the oral cavity, 1 ml of artificial saliva was added in a device at the start, and was added at a flow rate of 2 ml/min during the test. During the test, a force applied to the upper plunger 10 and a torque applied to the upper plunger 10 due to rotational sliding between the upper plunger 10 and the lower plunger 20 were measured by the sensor 12.

Figure 5A:
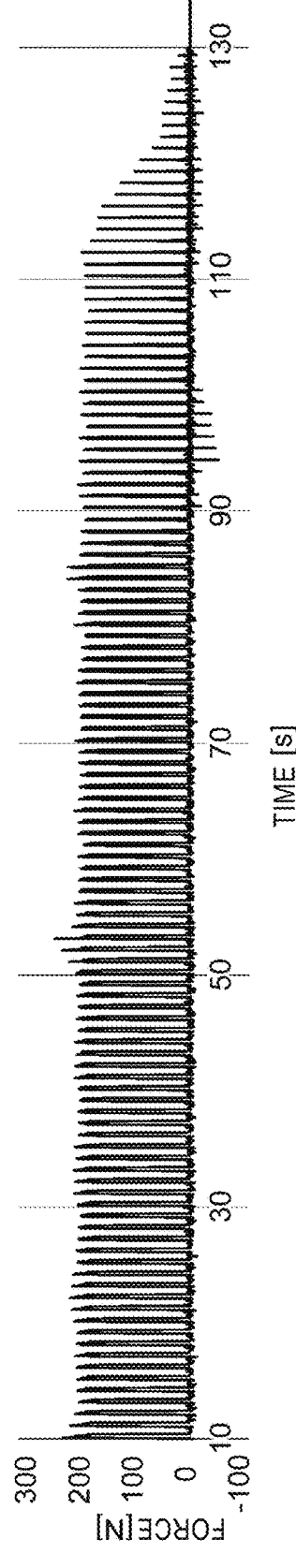
FIG. 5A is a graph showing an example of force data according to a first example.

FIG. 5A is a graph showing an example of the force data obtained by the food physical property evaluation device 1 in FIG. 1. FIG. 5A is a graph in which one peak appears in one compression. By integrating for each compression, an impulse value for each compression can be calculated. An impulse change profile during the test can be determined from a moving average of the impulses for every ten compressions.

Figure 5B:
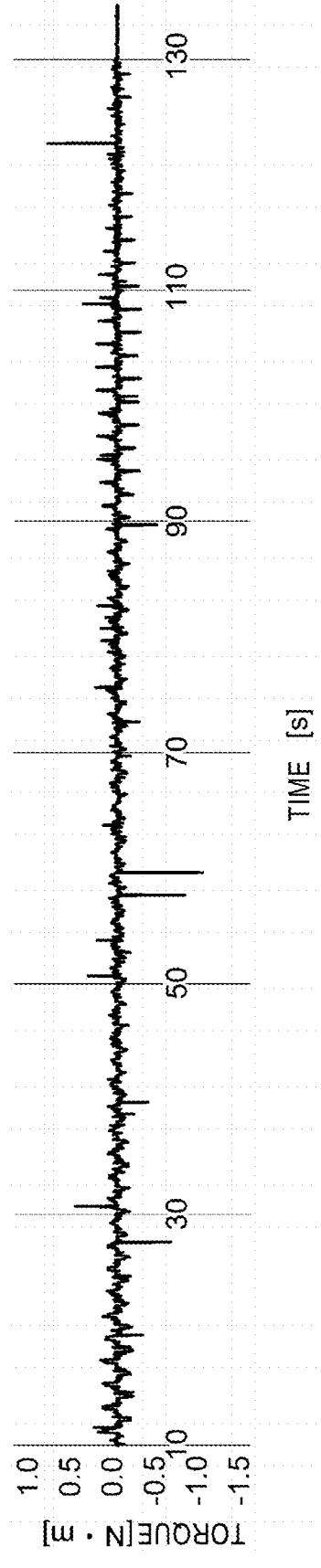
FIG. 5B is a graph showing an example of torque data according to the first example.

FIG. 5B is a graph showing an example of the torque data obtained by the food physical property evaluation device 1 in FIG. 1. Since rotation in the first rotation movement direction RR1 and rotation in the second rotation movement direction RR2 are alternately performed for each compression, the torques form a graph in which positive peaks and negative peaks alternately appear.

Figure 6:
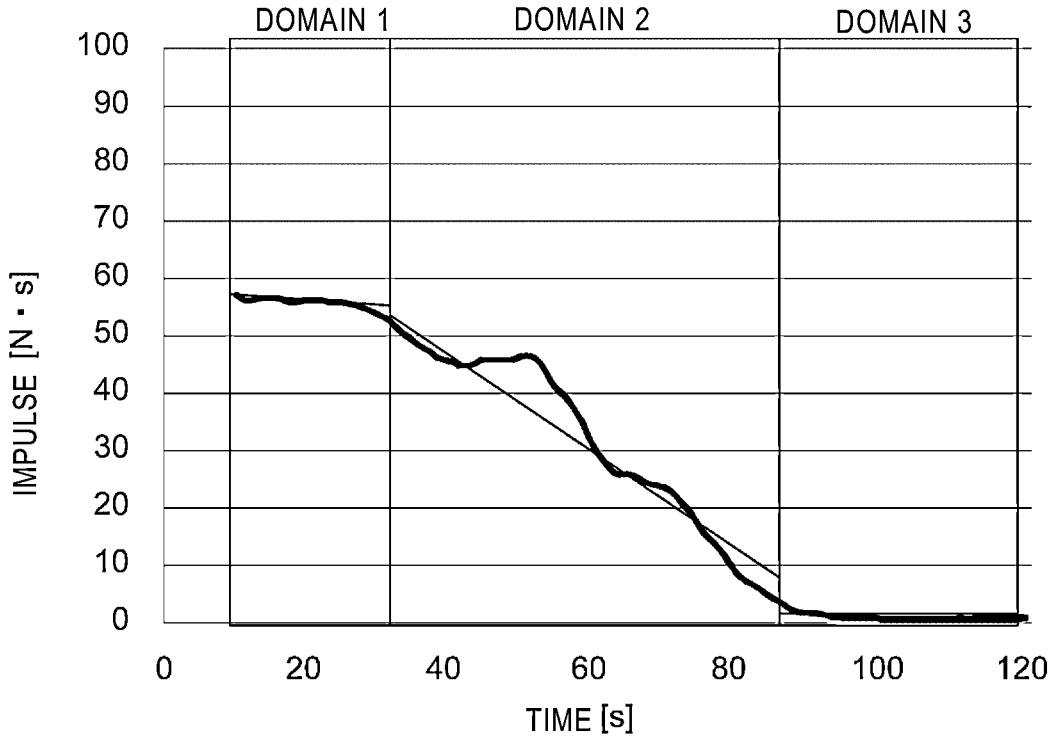
FIG. 6 is a graph showing a temporal change in an impulse according to the first example.

FIG. 6 is a graph showing a temporal change in the impulse obtained by the food physical property evaluation device 1 in FIG. 1. By integrating for each compression based on the force graph, the impulse value is calculated, and a profile of the temporal change in the impulse during the test is further obtained from the moving average of the impulses for every ten compressions.

In the graph of FIG. 6, a time domain can be divided into three parts, that is, a domain 1 in which the impulse is substantially constant (a slope is substantially zero); a domain 2 in which the impulse decreases (the slope is negative and is substantially constant); and a domain 3 in which the impulse is substantially unchanged (the slope is substantially zero). In each domain, a regression line in which the slope is substantially zero or the slope is negative and constant is shown.

The three domains of the profile of the temporal change in the impulse are estimated to correspond to stages of changes in properties of the chocolate, and can be described as follows. The domain 1 is a period when heat and a force are applied and surroundings are wet, but cutting, melting, and emulsification do not occur, or occur only locally. The domain 2 is a period when the cutting, the melting, and the emulsification begin to occur and overall "melting" occurs. The domain 3 is a period when the chocolate is completely melted and emulsified.

The entire profile of the temporal change in the impulse and feature data on each domain can be used as indices for physical property evaluation. Examples of the feature data on the entire profile of the temporal change in the impulse that can be the indices for the physical property evaluation include a maximum value, a minimum value, an average value, and a standard deviation. Examples of the feature data on the domain 1, the domain 2, and the domain 3 that can be the indices for the physical property evaluation include a maximum value, a minimum value, an average value, a slope of the regression line, and a domain time.

As described above, by dividing the time domain into domains in which behaviors with the temporal change in the impulse are different, and the food physical properties are evaluated based on the value of the impulse obtained for each domain.

Figure 7:
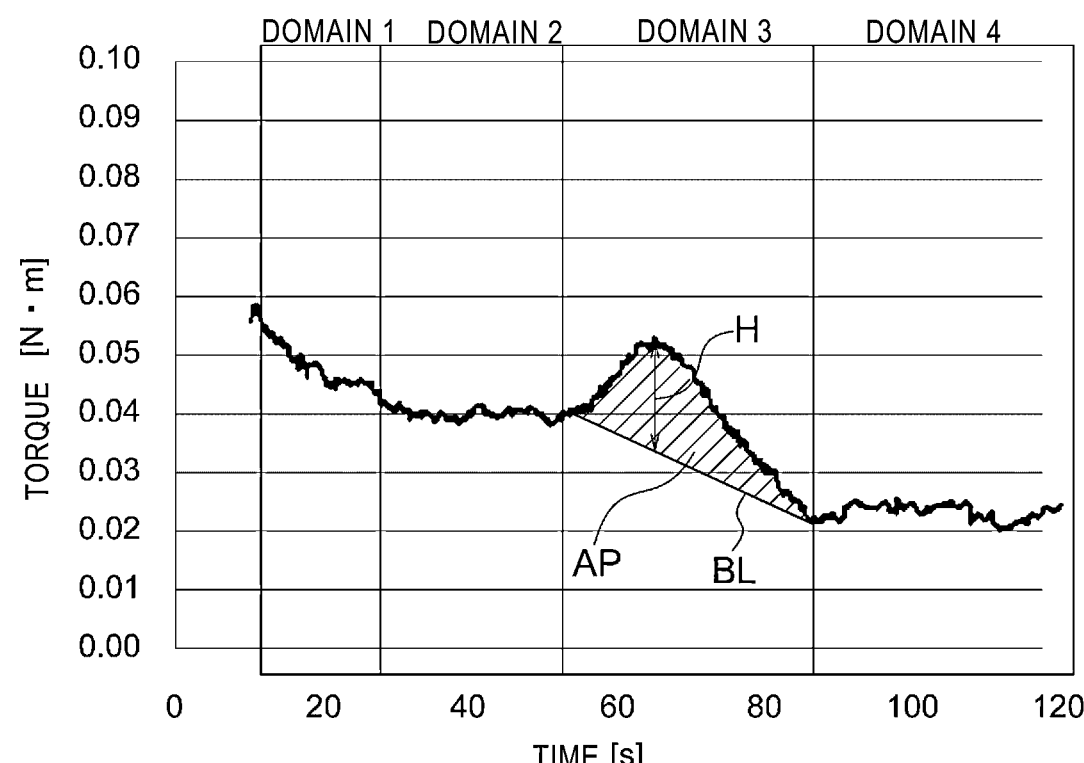
FIG. 7 is a graph showing a temporal change in an absolute value of a torque according to the first example.

FIG. 7 is a graph showing a temporal change in an absolute value of the torque obtained by the food physical property evaluation device 1 in FIG. 1. A profile of the temporal change in the torque during the test is obtained from a moving average of the torques for every ten compressions.

In the graph of FIG. 7, the time domain can be divided into four domains, that is, a domain 1 in which the torque decreases (the slope is substantially constant), a domain 2 in which the torque substantially does not change (the slope is substantially zero), a domain 3 in which the torque increases and reaches a peak and then decreases (the slope is positive and reaches a peak and then becomes negative), and a domain 4 in which the torque substantially does not change (the slope is substantially zero).

The four domains of the profile of the temporal change in the torque are estimated to correspond to stages of changes in properties of the chocolate, and can be described as follows. The domain 1 is a period when heat and a force are applied and surroundings are wet, but cutting, melting, and emulsification do not occur, or occur only locally. The domain 2 is a period when the cutting, the melting, and the emulsification begin to occur but only to a limited extent, and an increase in a contact area between the upper plunger 10 and lower plunger 20 is small. The domain 3 is a period when the contact area between the upper plunger 10 and the lower plunger 20 increases due to the cutting and the melting and thickening occurs due to mixing of the melted chocolate and a moisture, and subsequently, a resistance starts to decrease due to a progress of the melting and the emulsification. The domain 4 is a period when the chocolate is completely melted and emulsified. The domain 4 may not appear depending on the conditions of the test.

The entire profile of the temporal change in the torque and feature data on each domain can be used as indices for physical property evaluation. Examples of the feature data on the entire profile of the temporal change in the torque that can be the indices for the physical property evaluation include a maximum value, a minimum value, an average value, and a standard deviation. Examples of the feature data on the domain 1, the domain 2, and the domain 4 that can be the indices for the physical property evaluation include a maximum value, a minimum value, an average value, a slope of the regression line, and a domain time. Examples of the feature data on the domain 3 that can be the indices for the physical property evaluation include a maximum value, a minimum value, an average value, a slope of the regression line where the slope up to the peak is positive, a slope of the regression line where the slope is negative after the peak, a peak time, a height H of the peak from a baseline BL, and an integral value AP of the peak (an area of the domain between peak and the baseline BL). Here, the baseline BL is a straight line connecting a start point and an end point of the peak.

As described above, by dividing the time domain into domains in which behaviors with the temporal change in the torque are different, and the food physical properties are evaluated based on the value of the torque obtained for each domain.

Second Example

In the food physical property evaluation device 1 in the first embodiment, a test the same as that in the first example was performed on two types of commercially available chocolates (a chocolate CA and a chocolate CB, and each sample is about 2.5 g). During the test, a force and a torque applied to the upper plunger 10 by the sensor 12 were measured.

Figure 8:
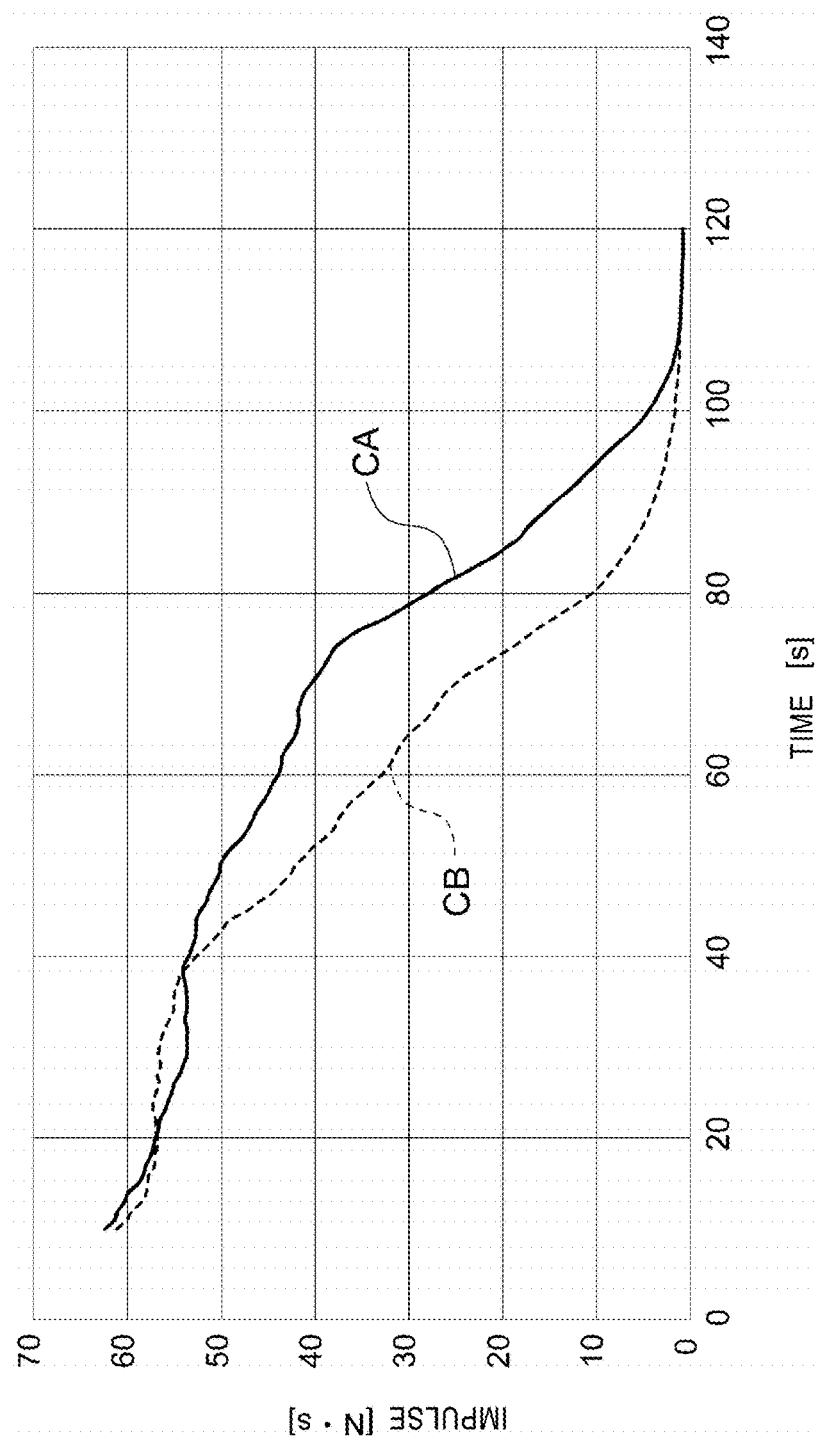
FIG. 8 is a graph showing a temporal change in an impulse according to a second example.

FIG. 8 is a graph showing a temporal change in the impulse obtained for two types of chocolates (the chocolate CA and the chocolate CB). By integrating for each compression based on the force graph, the impulse value was calculated, and a profile of the temporal change in the impulse during the test was further obtained from the moving average of the impulses for every ten compressions.

It was confirmed that the impulse of the chocolate CB starts to decrease earlier than that of the chocolate CA.

Figure 9:
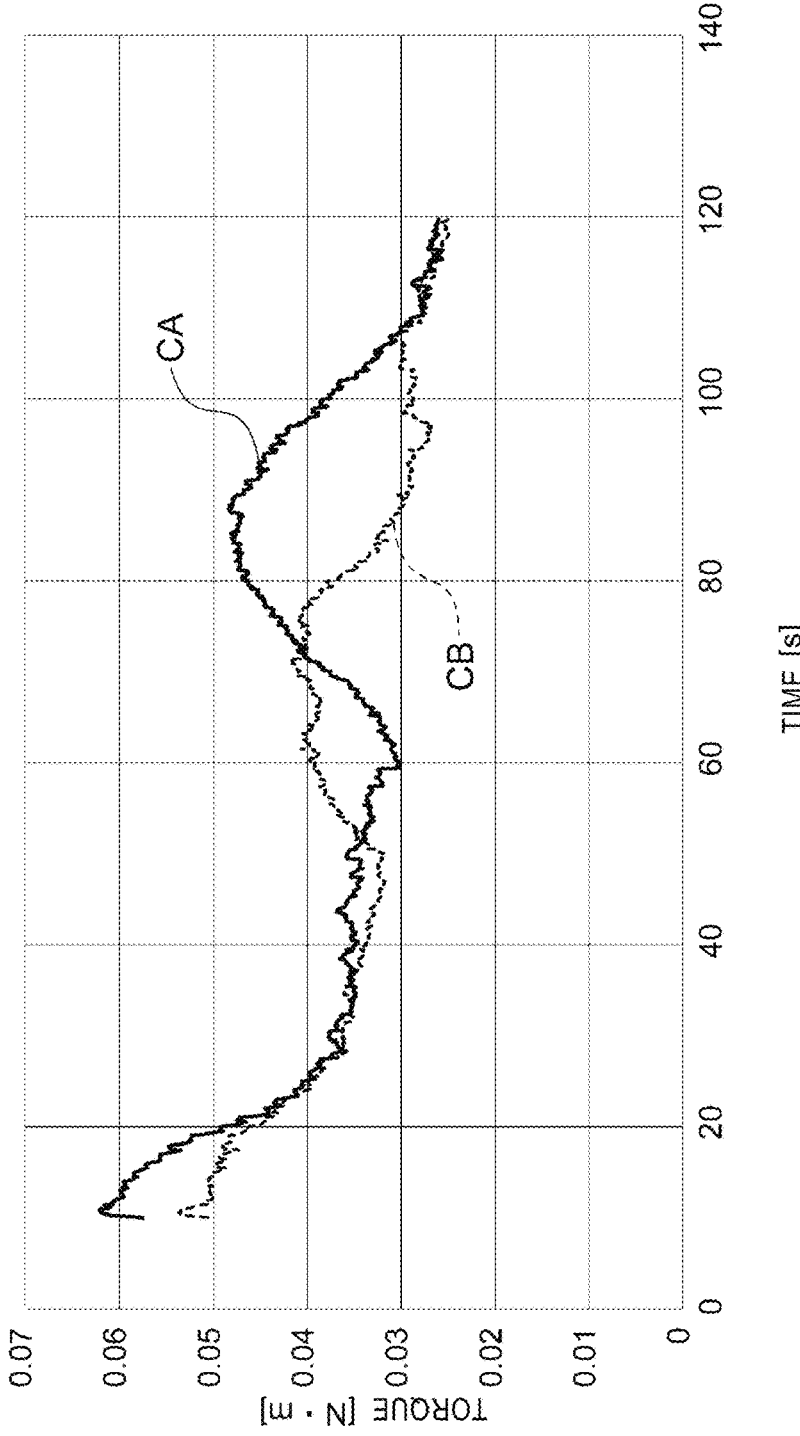
FIG. 9 is a graph showing a temporal change in an absolute value of a torque according to the second example.

FIG. 9 is a graph showing a temporal change in an absolute value of the torque obtained for two types of chocolates (the chocolate CA and the chocolate CB). A profile of the temporal change in the torque during the test was obtained from a moving average of the torques for every ten compressions.

It was confirmed that a peak position in the profile of the temporal change in the torque of the chocolate CB appears earlier than that of the chocolate CA.

To 11 specialized panels were given about 5.0 g of samples of two types of chocolates (the chocolate CA and the chocolate CB), followed by designating a eating method of "chewing ten times, then melting with an upper jaw and a tongue as in a grinding manner and swallowing", and thereafter, for each item of a "melting speed", a "sticky feeling", an "ease of spread in mouth", and a "state in mouth after swallowing", evaluation was performed in seven stages of +3 points, +2 points, +1 point, 0 points, −1 points, −2 points, and −3 points from high evaluation to low evaluation.

Figure 10:
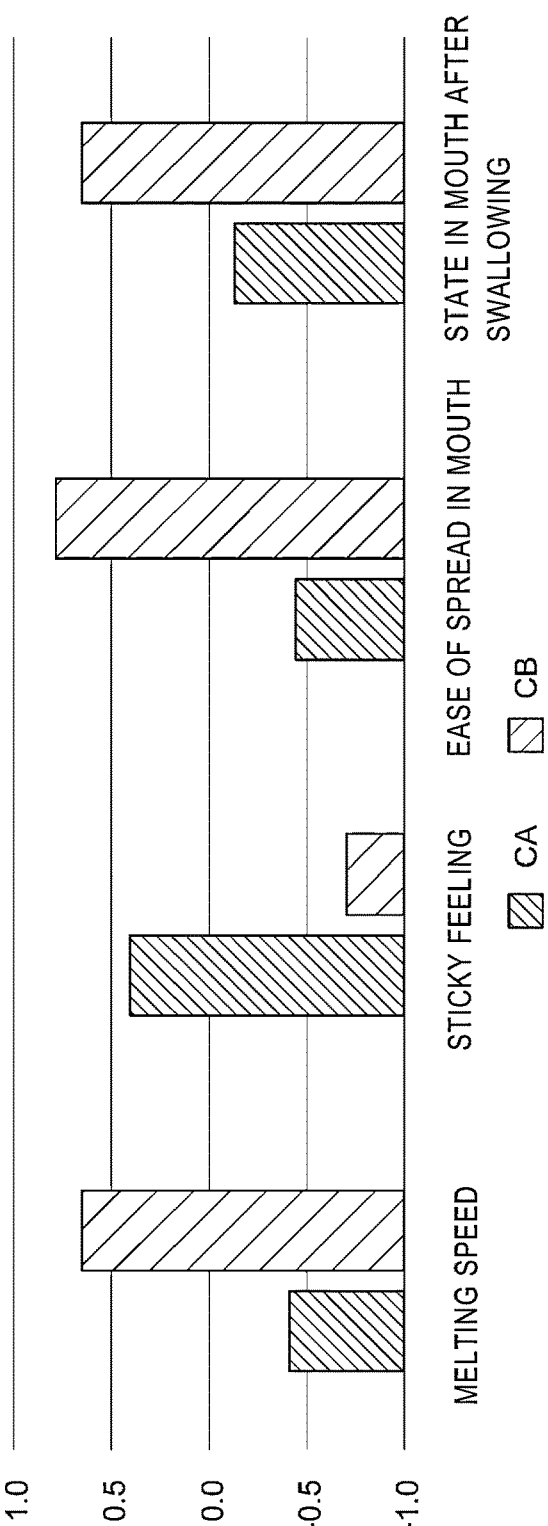
FIG. 10 is a graph showing a food texture sensory evaluation result according to the second example.

FIG. 10 is a graph showing a food texture sensory evaluation result. Scores are shown for each item of the "melting speed", the "sticky feeling", the "ease of spread in mouth", and the "state in mouth after swallowing" for two types of chocolates (the chocolate CA and the chocolate CB). According to the food texture sensory evaluation result, compared to the chocolate CA, the chocolate CB melts faster, has no sticky feeling, spreads easily in the mouth, and results in a dry state in mouth after swallowing.

The above-described food texture sensory evaluation result can be estimated by associating the feature data on the profile of the temporal change in the impulse in FIG. 8 and the profile of the temporal change in the torque in FIG. 9 with each other as follows.

Figure 11:
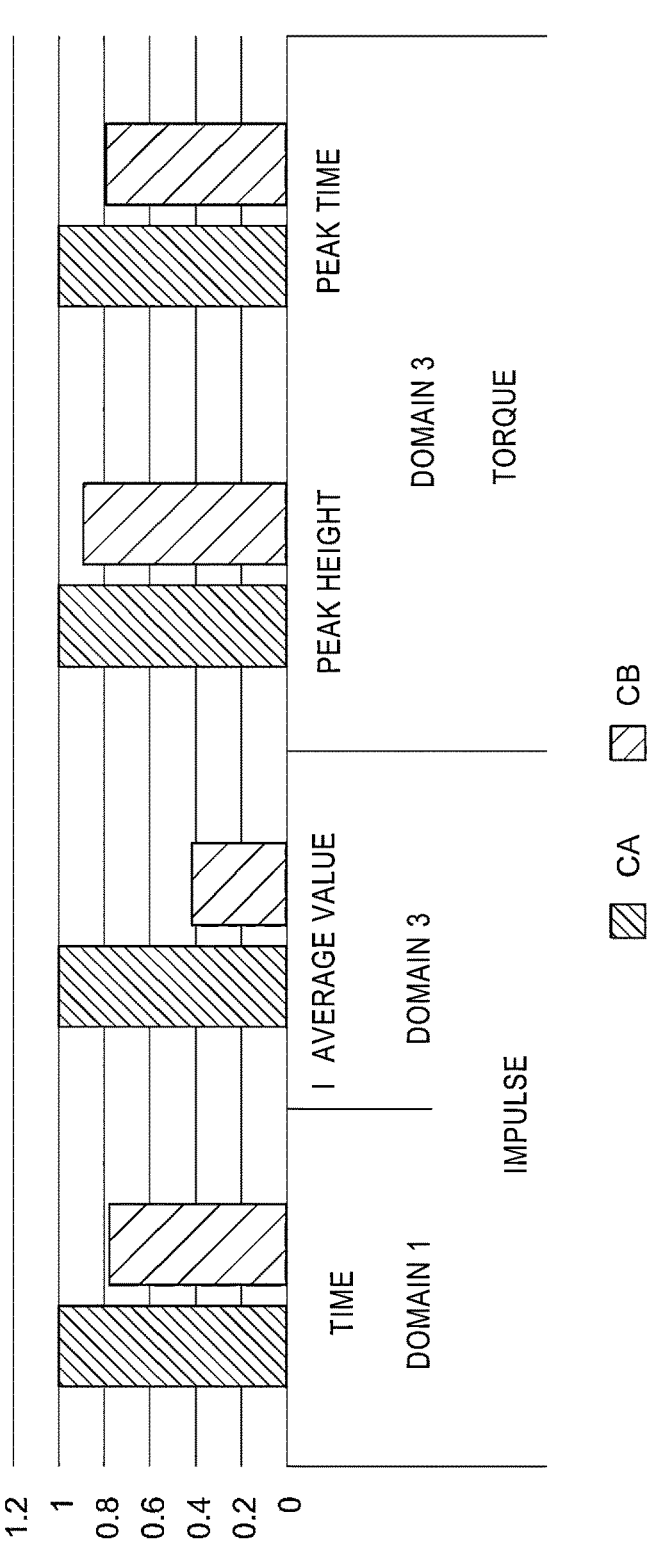
FIG. 11 is a graph showing a physical property measurement result according to the second example.

FIG. 11 is a graph showing a physical property measurement result according to the second example. The "melting speed" has a negative correlation with the domain 1 of the impulse. The "sticky feeling" has a positive correlation with a peak height in the domain 3 of the torque, or a positive correlation with a peak time. It is considered that the chocolate changes from an oil continuous phase to a water continuous phase just before swallowing, and a consistency increases during the phase change and the chocolate becomes sticky. The "ease of spread in mouth" has a negative correlation with a peak height in the domain 3 of the torque or a negative correlation with a peak time. The "state in mouth after swallowing" has a negative correlation with an average value of the impulses in the domain 3.

The data measured as the food physical properties coincided with the result of the sensory test, and a sensory test result that can match the state of the chocolate estimated based on the temporal change in the impulse and the temporal change in the torque was obtained.

Second Embodiment

A food physical property evaluation device according to the embodiment has a configuration the same as that of the food physical property evaluation device 1 according to the first embodiment except that an upper plunger 60 and a lower plunger 70 have the following configurations.

The upper plunger 60 and the lower plunger 70 according to the embodiment are intraoral models having shapes suitable for evaluation of physical properties of a chocolate snack, and the food physical property evaluation device according to the embodiment can be suitably used particularly for evaluation of the physical properties of a chocolate snack.

Figure 12A:
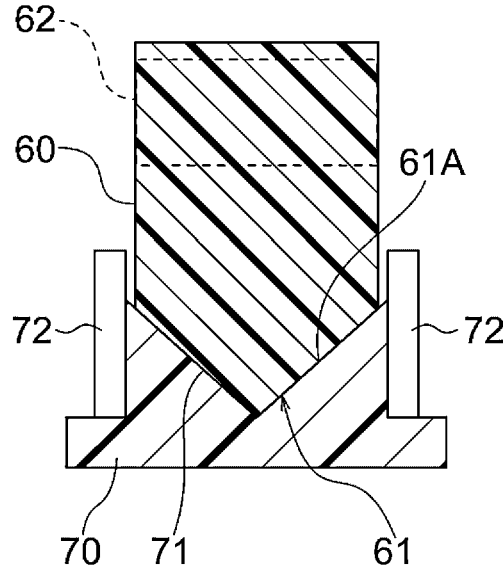
FIG. 12A is a schematic view showing a configuration of a food physical property evaluation device according to a second embodiment in a state in which an upper plunger and a lower plunger are occluded when viewed from one direction.

FIG. 12A is a schematic view showing a configuration of the food physical property evaluation device according to the embodiment in a state in which the upper plunger 60 and the lower plunger 70 are occluded when viewed from one direction. An upper occlusal part 61 is provided at a tip end of the upper plunger 60. The upper occlusal part 61 has a shape in which convex portions and concave portions are alternately disposed in a circumferential direction, and for example, four convex portions and four concave portions therebetween are alternately disposed in the circumferential direction. FIG. 12A shows a shape of a first convex portion 61A, which is one of the four convex portions.

The lower plunger 70 is provided such that a lower occlusal part 71 having a shape to be occluded with the upper occlusal part 61 faces the upper occlusal part 61. The lower occlusal part 71 has a shape provided with a convex-concave shape corresponding to a position to be occluded with a concave-convex shape of the upper occlusal part 61.

Figure 12B:
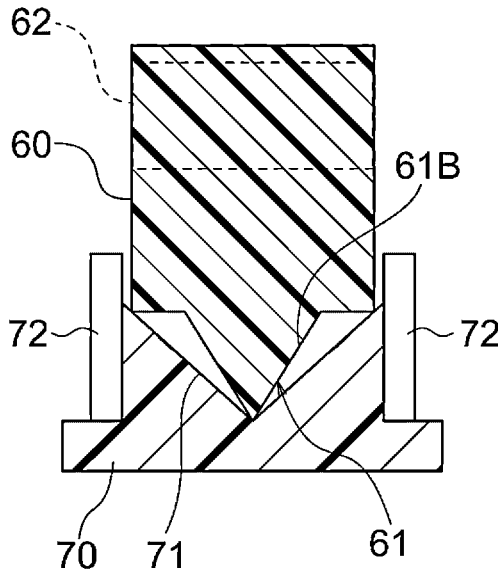
FIG. 12B is a schematic view showing a configuration of the food physical property evaluation device in FIG. 12A in the state in which the upper plunger and the lower plunger are occluded when viewed from another direction orthogonal to the one direction.

FIG. 12B is a schematic view showing a configuration of the food physical property evaluation device in FIG. 12A in the state in which the upper plunger 60 and the lower plunger 70 are occluded when viewed from another direction orthogonal to the one direction. FIG. 12A shows a shape of a second convex portion 61B, which is one of the four convex portions. The second convex portion 61B is a convex portion whose tip end is sharper than the first convex portion 61A.

The upper occlusal part 61 of the upper plunger 60 in the embodiment has a shape in which the first convex portion 61A and the second convex portion 61B are alternately disposed in the circumferential direction. That is, the first convex portion 61A extending in one direction and the second convex portion 61B extending in a direction orthogonal to the one direction intersect in a cross shape. On the other hand, the lower occlusal part 71 of the lower plunger 70 has a shape in which concave portions and convex portions are alternately disposed in the circumferential direction, which coincides with or is close to the shape of the first convex portion 61A that is more obtuse than the second convex portion 61B. According to the above configuration, when the second convex portion 61B of the upper occlusal part 61 and the lower occlusal part 71 are occluded, although surfaces of the first convex portion 61A and a concave-convex-shaped surface of the lower occlusal part 71 are occluded with no or almost no gap therebetween, a gap is generated between surfaces of the second convex portion 61B and the concave-convex-shaped surface of the lower occlusal part 71.

As in the first embodiment, a sensor 62 is incorporated in the upper plunger 60, and measures a physical quantity applied to the upper plunger 60. For example, a cylindrical protective part 72 is provided on an outer circumference of the lower plunger 70.

The lower plunger 70 having the above configuration is provided so as to be capable of reciprocating linear movement in the linear direction in which the lower plunger 70 is to be occluded with the upper plunger 60 as in the first embodiment, and the upper plunger 60 is provided so as to be capable of reciprocating rotation movement with a direction of the reciprocating linear movement of the lower plunger 70 as a rotation axis.

The upper occlusal part 61 of the upper plunger 60 can be occluded most deeply at a position at which the upper occlusal part 61 can be occluded with the lower occlusal part 71, that is, in an arrangement in which positions of most protruding tip ends of the convex portions of the upper plunger 60 and positions of most concave portions of the concave portions of the lower plunger 70 coincide with each other.

In addition, the lower plunger 70 may be occluded with the upper plunger 60 at a position shifted in the circumferential direction from the arrangement in which the positions of the most protruding tip ends of the convex portions of the upper plunger 60 and the positions of the most concave portion of the concave portions of the lower plunger 70 coincide with each other. Operations of the upper plunger 60 in this case will be described later.

Figure 13:
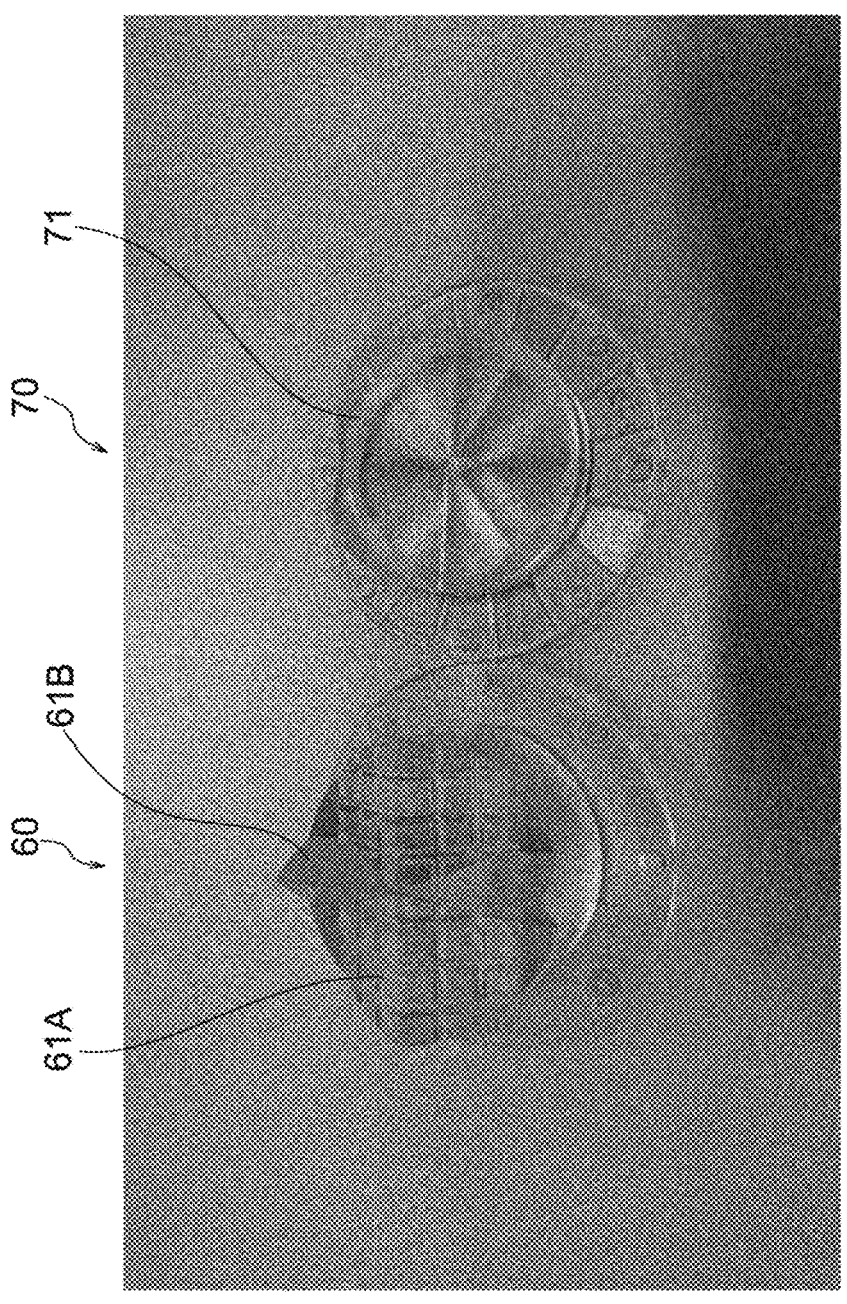
FIG. 13 is a photograph showing an example of the upper plunger and the lower plunger of the food physical property evaluation device in FIG. 12A.

FIG. 13 is a photograph showing an example of the upper plunger 60 and the lower plunger 70 of the food physical property evaluation device according to the embodiment. The upper plunger 60 is provided with the upper occlusal part 61 including the first convex portions 61A and the second convex portions 61B. The lower plunger 70 is provided with the lower occlusal part 71 having a concave-convex shape to be occluded with the upper occlusal part 61.

Next, a food physical property evaluation method according to the embodiment will be described. First, regarding a relative position of the upper plunger 60 and the lower plunger 70 in the circumferential direction, a case will be described in which the upper occlusal part 61 of the upper plunger 60 is occluded at a position at which the upper occlusal part 61 can be occluded most deeply with the lower occlusal part 71, that is, in an arrangement in which the positions of most protruding tip ends of the convex portions of the upper plunger 60 and the positions of most concave portions of the concave portions of the lower plunger 70 coincide with each other.

Figure 14A:
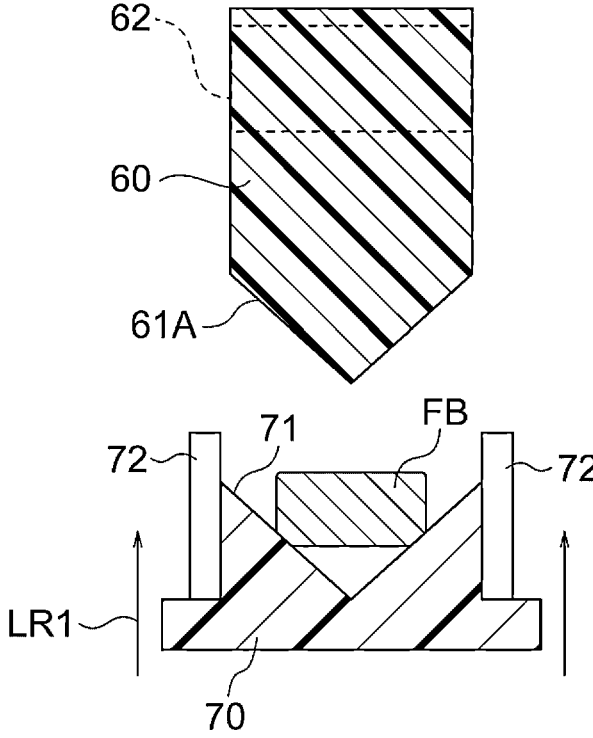
FIG. 14A is a schematic view of an example of operations of the upper plunger and the lower plunger of the food physical property evaluation device in FIG. 12A when viewed from one direction.

FIG. 14A is a schematic view of an example of operations of the upper plunger 60 and the lower plunger 70 of the food physical property evaluation device in FIG. 12A when viewed from the one direction. As in the first embodiment, a food FB to be evaluated is placed on the lower occlusal part 71. Next, the lower plunger 70 is elevated in the first linear movement direction LR1, and the lower occlusal part 71 of the lower plunger 70 occludes with the upper occlusal part 61 of the upper plunger 60.

Figure 14B:
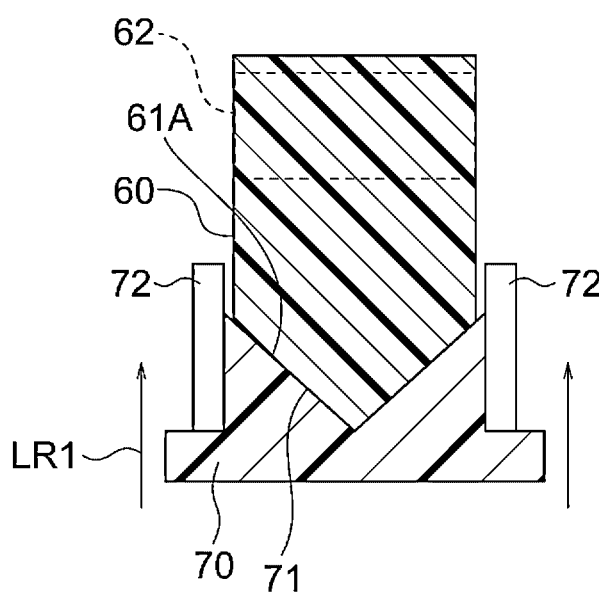
FIG. 14B is a schematic view showing an operation subsequent to FIG. 14A.

Next, as shown in FIG. 14B, when the lower occlusal part 71 of the lower plunger 70 occludes with the upper occlusal part 61 of the upper plunger 60, the food FB is pressed into a gap between the lower occlusal part 71 and the upper occlusal part 61 with a predetermined force.

Figure 14C:
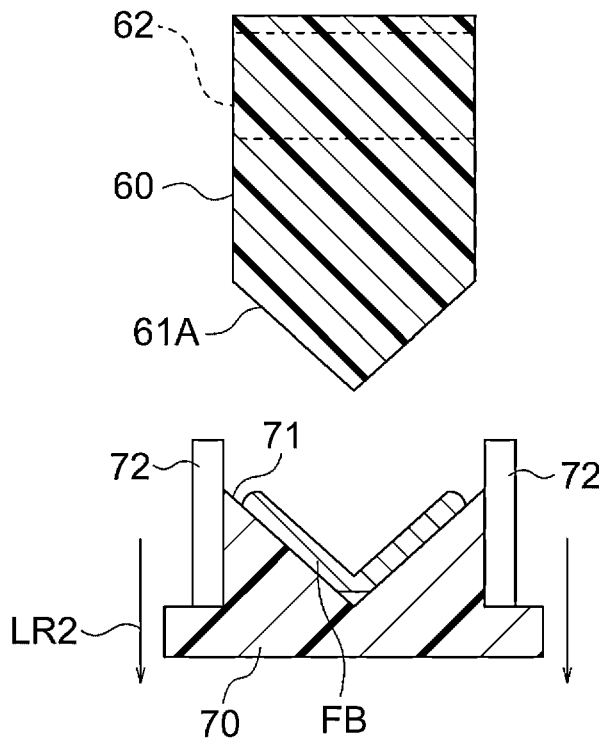
FIG. 14C is a schematic view showing an operation subsequent to FIG. 14B.

Subsequently, as shown in FIG. 14C, the lower plunger 70 is lowered in the second linear movement direction LR2, and the occlusion between the lower occlusal part 71 of the lower plunger 70 and the upper occlusal part 61 of the upper plunger 60 is released. Since the surfaces of the first convex portions 61A and the concave-convex-shaped surface of the lower occlusal part 71 are occluded with no or almost no gap therebetween, the food FB is crushed to have a uniform thickness.

Figure 14D:
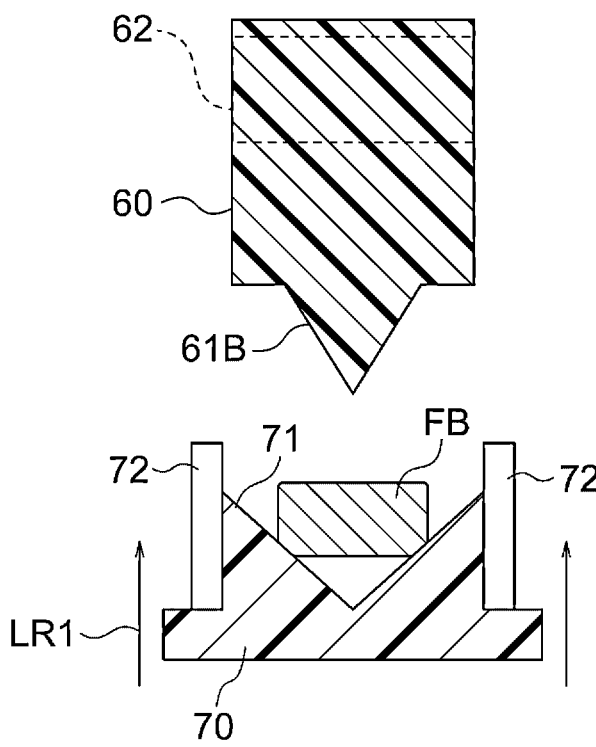
FIG. 14D is a schematic view of the operations in FIG. 14A when viewed from another direction.

Operations when the above operations are viewed from the other direction orthogonal to the one direction will be described. FIG. 14D is a schematic view of an example of the operations of the upper plunger 60 and the lower plunger 70 of the food physical property evaluation device in FIG. 12A as viewed from the other direction orthogonal to the one direction. The food FB to be evaluated is placed on the lower occlusal part 71, the lower plunger 70 is elevated in the first linear movement direction LR1, and the lower occlusal part 71 of the lower plunger 70 occludes with the upper occlusal part 61 of the upper plunger 60.

Figure 14E:
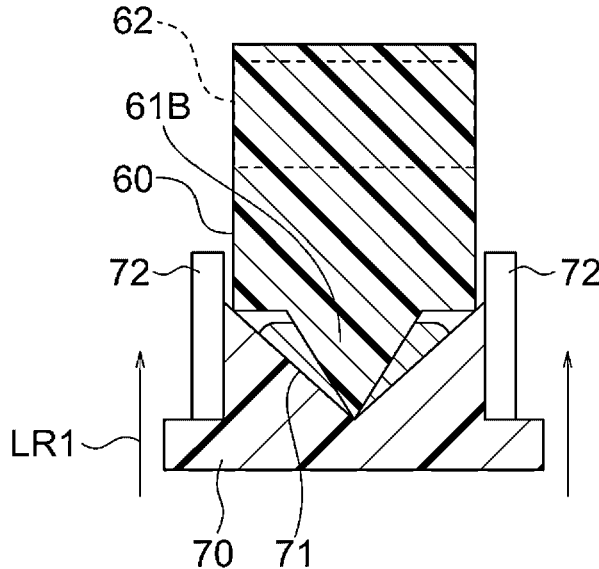
FIG. 14E is a schematic view showing an operation subsequent to FIG. 14D.

Next, as shown in FIG. 14E, when the lower occlusal part 71 of the lower plunger 70 occludes with the upper occlusal part 61 of the upper plunger 60, the food FB is pressed into a gap between the lower occlusal part 71 and the upper occlusal part 61 with a predetermined force.

Figure 14F:
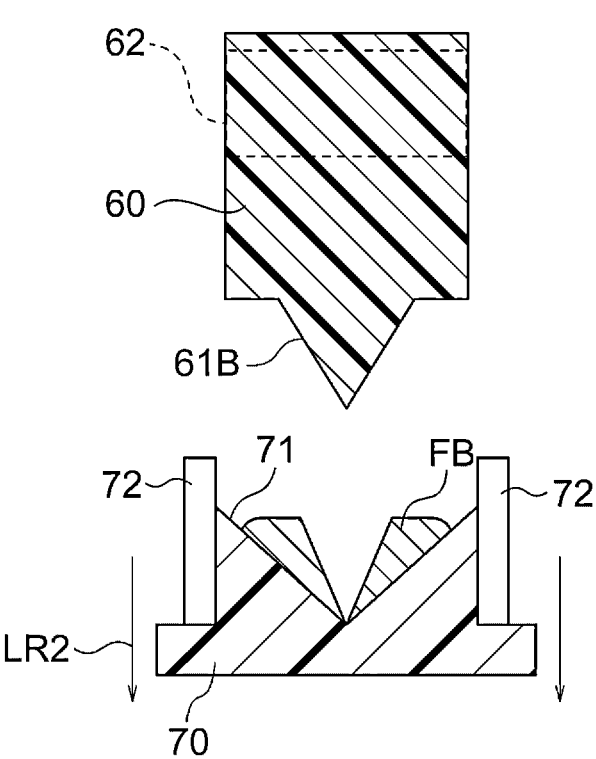
FIG. 14F is a schematic view showing an operation subsequent to FIG. 14E.

Subsequently, as shown in FIG. 14F, the lower plunger 70 is lowered in the second linear movement direction LR2, and the occlusion between the lower occlusal part 71 of the lower plunger 70 and the upper occlusal part 61 of the upper plunger 60 is released. Since the surfaces of the second convex portions 61B and the concave-convex-shaped surface of the lower occlusal part 71 are occluded with a gap therebetween, the food FB is cut at the center.

Next, regarding a relative position of the upper plunger 60 and the lower plunger 70 in the circumferential direction, a case will be described in which the lower plunger 70 is occluded with the upper plunger 60 at a position shifted in the circumferential direction from the arrangement in which the positions of the most protruding tip ends of the convex portions of the upper plunger 60 and the positions of the most concave portions of the concave portions of the lower plunger 70 coincide with each other.

Figure 14G:
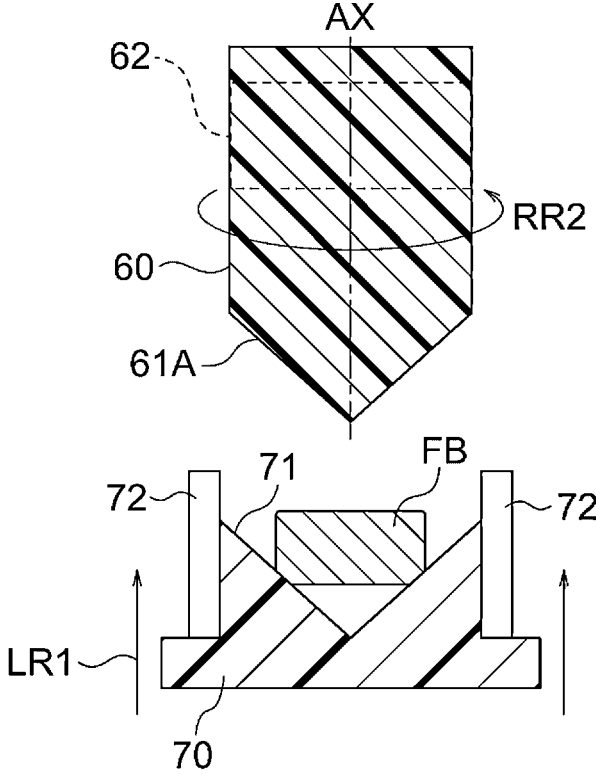
FIG. 14G is a schematic view of another example of the operations of the upper plunger and the lower plunger of the food physical property evaluation device in FIG. 12A when viewed from one direction.

FIG. 14G is a schematic view of an example of the operations of the upper plunger 60 and the lower plunger 70 of the food physical property evaluation device in FIG. 12A when viewed from the one direction. As in the first embodiment, the food FB to be evaluated is placed on the lower occlusal part 71. Next, the lower plunger 70 is elevated in the first linear movement direction LR1, and the lower occlusal part 71 of the lower plunger 70 occludes with the upper occlusal part 61 of the upper plunger 60. Here, the upper plunger 60 rotates in the second rotation movement direction RR2 (or the first rotation movement direction RR1), and the lower plunger 70 is occluded with the upper plunger 60 at a position shifted in the circumferential direction from the arrangement in which the positions of the most protruding tip ends of the convex portions of the upper plunger 60 and the positions of the most concave portions of the concave portions of the lower plunger 70 coincide with each other.

Figure 14H:
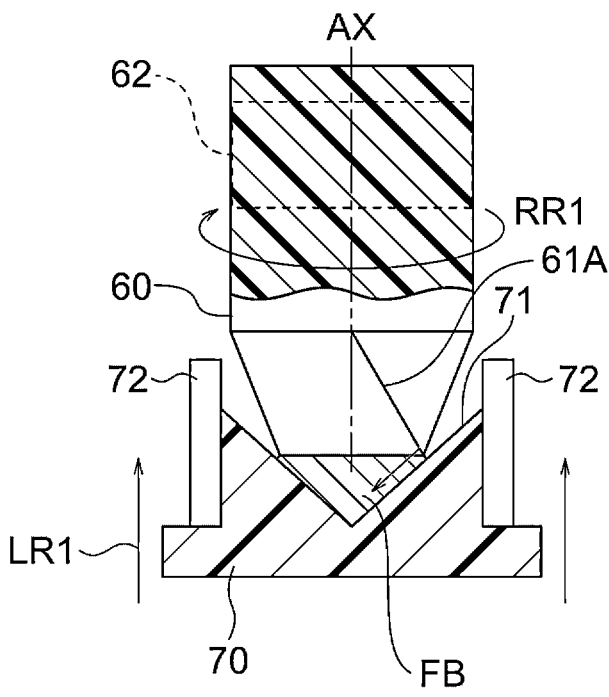
FIG. 14H is a schematic view showing an operation subsequent to FIG. 14G.

Next, as shown in FIG. 14H, the tip ends of the convex portions (the first convex portion 61A or the second convex portion 61B) of the upper occlusal part 61 are in contact with inclined surfaces constituting the concave portions and the convex portions of the lower occlusal part 71. In this state, by elevating the lower plunger 70 in the first linear movement direction LR1 to occlude with the upper plunger 60 with the lower plunger 70, while the upper plunger 60 is rotated in the first rotation movement direction RR1, the tip ends of the convex portions (the first convex portions 61A or the second convex portions 61B) of the upper occlusal part 61 are slid on the inclined surfaces constituting the concave portions and the convex portions of the lower occlusal part 71. Accordingly, the upper occlusal part 61 of the upper plunger 60 slides while being in contact with the food FB. Here, it is described that the tip ends of the convex portions of the upper occlusal part 61 are slid on the inclined surfaces while rotating the upper plunger 60 in the first rotation movement direction RR1, and the tip ends of the convex portions of the upper occlusal part 61 may be slid on the inclined surfaces while rotating in the second rotation movement direction RR2. A direction in which the tip ends of the convex portions of the upper occlusal part 61 slide on the inclined surfaces constituting the concave portions and the convex portions of the lower occlusal part 71 is a direction in which the positions of the most protruding tip ends of the convex portions of the upper occlusal part 61 and the positions of the most concave portions of the concave portions of the lower occlusal part 71 coincide with each other. In addition, a configuration may be adopted in which the sliding of the tip ends of the convex portions of the upper occlusal part 61 on the inclined surfaces is performed on at least a part of the inclined surfaces. In addition, the sliding may be performed until the positions of the most protruding tip ends of the convex portions of the upper occlusal part 61 and the positions of the most concave portions of the concave portions of the lower occlusal part 71 coincide with each other.

The upper plunger 60 and the lower plunger 70 are disposed at positions where the upper plunger 60 and the lower plunger 70 are not in contact with each other even when the upper plunger 60 and the lower plunger 70 are closest to each other in an arrangement in which the positions of the tip ends of the convex portions of the upper occlusal part 61 and the positions of the most concave portions of the concave portions of the lower occlusal part 71 coincide with each other. When the food FB to be evaluated is present on the lower occlusal part 71, a force corresponding to a set compression force is applied from the lower plunger 70 to the food FB, and is further applied to the upper plunger 60 via the food FB. During the occlusion of the upper plunger 60 and the lower plunger 70, a force exceeding the set compression force is not applied.

In the food physical property evaluation device according to the embodiment, as described above, in the case of occlusion at a position shifted in the circumferential direction from the arrangement in which the positions of the most protruding tip ends of the convex portions of the upper occlusal part 61 and the positions of the most concave portions of the concave portions of the lower occlusal part 71 coincide with each other, the tip ends of the convex portions (the first convex portions 61A or the second convex portions 61B) of the upper occlusal part 61 can come into contact with the inclined surfaces constituting the concave portions and the convex portions of the lower occlusal part 71.

Figure 14I:
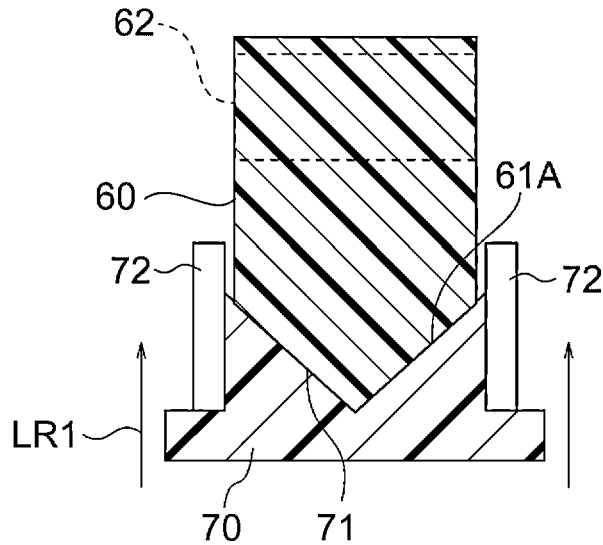
FIG. 14I is a schematic view showing an operation subsequent to FIG. 14H.
Figure 14J:
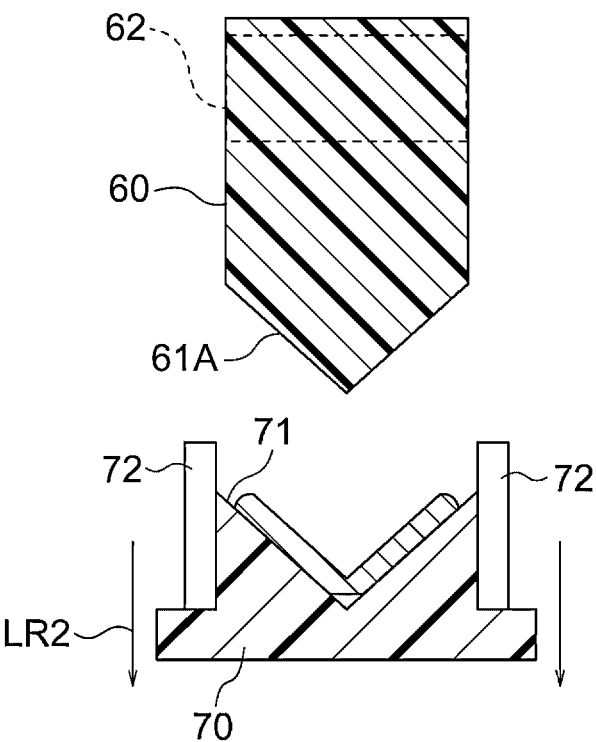
FIG. 14J is a schematic view showing an operation subsequent to FIG. 14I.

Next, as shown in FIG. 14I, after the occlusion until the positions of the convex portions of the upper plunger 60 coincide with the positions of the concave portions of the lower plunger 70, as shown in FIG. 14J, the lower plunger 70 is lowered in the second linear movement direction LR2, and the occlusion of the lower occlusal part 71 of the lower plunger 70 and the upper occlusal part 61 of the upper plunger 60 is released.

In the food physical property evaluation method according to the embodiment, the operations of FIGS. 14G to 14J are included. Only the operations of FIGS. 14G to 14J may be repeated. At this time, an angle of the upper plunger 60 under the arrangement in which the positions of the convex portions of the upper plunger 60 and the positions of the concave portions of the lower plunger 70 coincide with each other may be rotated by 90° each time one or more compression steps are completed. When performing the above-described operations including FIGS. 14A to 14C (or FIGS. 14D to 14F as viewed from the orthogonal direction), the upper plunger 60 is rotated by 90° each time one or more compression steps are completed, and an angle at which the upper occlusal part 61 is in contact with the food FB during the occlusion can be changed. After performing the operations of FIGS. 14A to 14C (or FIGS. 14D to 14F as viewed from the orthogonal direction) for one or more compression steps, the operations of FIGS. 14G to 14J may be performed for one or more compression steps. After performing the operations of FIGS. 14G to 14J for one or more compression steps, the operations of FIGS. 14A to 14C (or FIGS. 14D to 14F as viewed from the orthogonal direction) may be performed for one or more compression steps. Further, one or more compression steps of the operations of FIGS. 14A to 14C (or FIGS. 14D to 14F as viewed from the orthogonal direction) and one or more compression steps of the operations of FIGS. 14G to 14J may be alternately repeated. In addition, the operations of FIGS. 14A to 14C (or FIGS. 14D to 14F as viewed from the orthogonal direction) and the operations of FIGS. 14G to 14J can be appropriately combined.

A food suitable for evaluation of the food physical property evaluation device in the embodiment is a chocolate snack. The chocolate snack is, for example, a snack made of chocolate containing a puff. Various types of puffs can be used, and the puff is preferably a soybean puff, and more preferably a puff made by soybean protein. The soybean puff is obtained by puffing the soybean protein as a main ingredient, and the soybean protein is obtained by puffing a soybean protein concentrated ingredient.

The operations of the upper plunger 60 and the lower plunger 70 of the food physical property evaluation device according to the embodiment shown in FIGS. 14G to 14J described above simulate a grinding behavior of teeth in an oral cavity. According to the food physical property evaluation device in the embodiment, it is possible to simulate the grinding behavior of the teeth to simulate the change in the food properties in the oral cavity, and to obtain the physical quantity corresponding to perception in the oral cavity. For example, a force (an impulse obtained when integrated) and a torque are obtained for the food to be evaluated. In addition, it is possible to obtain the temporal change in the physical quantity corresponding to the perception in the oral cavity with respect to the food to be evaluated. For example, a temporal change in the force (the impulse obtained when integrated) and a temporal change in the torque are obtained with respect to the food to be evaluated. The food physical properties can be evaluated based on these pieces of data.

In the related art, an intraoral model that continuously simulates a cutting behavior by the teeth and a grinding behavior of the teeth is not known. In the food physical property evaluation device according to the embodiment, by continuously simulating the cutting behavior by the teeth and the grinding behavior of the teeth, reproducibility of the change in the food properties in the oral cavity can be enhanced, and the physical quantity corresponding to the perception in the oral cavity can be obtained.

In particular, in the food physical property evaluation device according to the embodiment, by measuring the torque applied to the upper plunger 60 or the lower plunger 70, it is possible to obtain the physical quantity corresponding to a feeling of the sliding behavior of the tongue. In addition, in the food physical property evaluation device according to the embodiment, since the reciprocating linear movement is performed in a vertical direction, an actual movement in the oral cavity can be more accurately modeled.

Third Example

In the food physical property evaluation device according to the second embodiment, about 8.0 g of a chocolate snack sample was used, and a test was conducted in which the upper plunger 60 and the lower plunger 70 were driven. The treatment was performed with a compression force of 400 N, a number of compression of 60 times, and a compression frequency of 49 times/minute. A temperature of a plunger surface in contact with the chocolate snack was adjusted to 33° C. to 35° C. In order to simulate saliva retained in the oral cavity, 0.7 ml of artificial saliva was added in a device at the start, and was added at a flow rate of 4 ml/min during the test. Among 60 times of compression, the first to tenth times are the compression shown in the operations of FIGS. 14A to 14C (FIGS. 14D to 14F), and the 11th to 60th times thereafter are the compression including the operations simulating the grinding behavior of the teeth shown in FIGS. 14G to 14J. During the test, a force applied to the upper plunger 60 was measured by the sensor 62, and an impulse was calculated based on the obtained force.

Figure 15A:
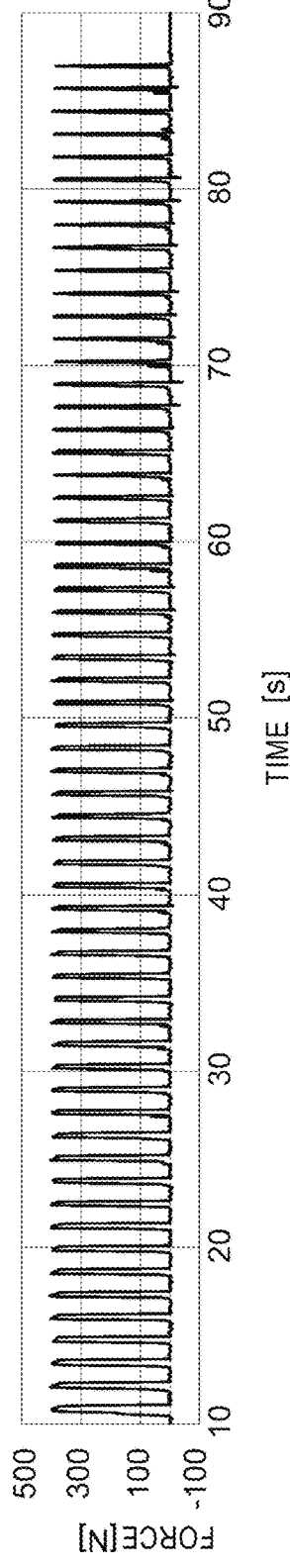
FIG. 15A is a graph showing an example of force data according to a third example.

FIG. 15A is a graph showing an example of force data obtained by the food physical property evaluation device in FIG. 12A. FIG. 15A is a graph in which one peak appears in one compression. By integrating for each compression, an impulse value for each compression can be calculated. An impulse change profile during the test can be determined from a moving average of the impulses for every ten compressions.

Figure 15B:
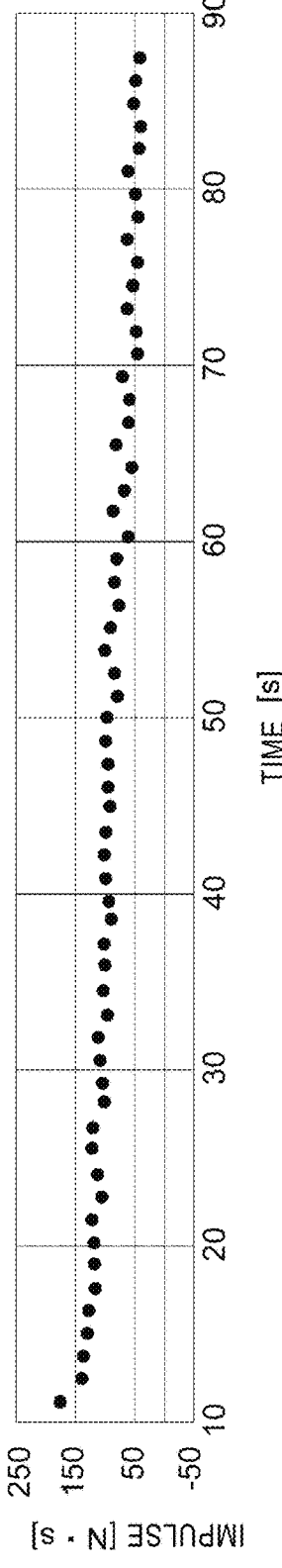
FIG. 15B is a graph showing an example of impulse data according to the third example.

FIG. 15B is a graph showing an example of impulse data obtained by the food physical property evaluation device in FIG. 12A. By integrating for each compression based on FIG. 15A, the impulse value for each compression can be calculated.

Fourth Example

In the food physical property evaluation device in the second embodiment, a test the same as that in the third example was performed on two types of commercially available chocolate snacks (a chocolate snack CSA and a chocolate snack CSB, and each sample is about 8.0 g). During the test, a force applied to the upper plunger 60 by the sensor 62 was measured.

Here, the chocolate snack CSA and the chocolate snack CSB are both protein-rich chocolate snacks, and the chocolate snack CSA uses a flour ingredient as a main protein ingredient, and the chocolate snack CSB uses a soybean puff as the main protein ingredient.

Figure 16:
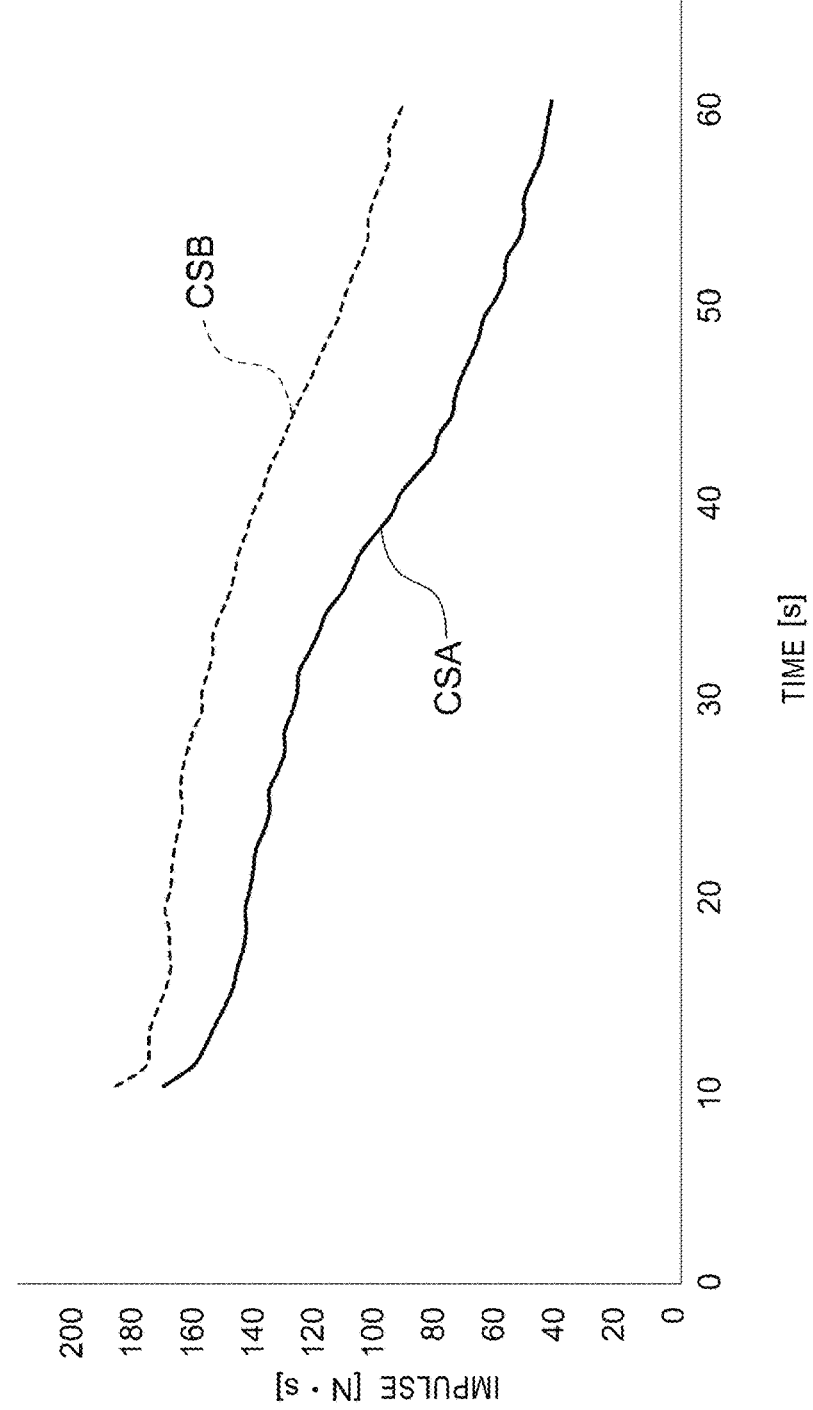
FIG. 16 is a graph showing a temporal change in an impulse according to a fourth example.

FIG. 16 is a graph showing a temporal change in the impulse obtained for two types of chocolate snacks (the chocolate snack CSA and the chocolate snack CSB). By integrating for each compression based on the force graph, the impulse value was calculated, and a profile of the temporal change in the impulse during the test was further obtained from a moving average of the impulses for every ten compressions.

It was confirmed that the impulse of the chocolate snack CSB is longer in a higher domain than the chocolate snack CSA and continues throughout the test time. A soybean puff is a processed food containing a soybean protein as a main ingredient, and by using the soybean puff as a confectionery, it is possible to increase a protein content of a product and to impart a crispy and crunchy food texture. Since the chocolate snack CSB contains the soybean puff, it is considered that the impulse value at an early stage of mastication is large. Further, in latter half of the mastication, the chocolate snack CSA is melted by mixing with saliva, whereas in the case of the chocolate snack CSB, it is considered that crispness and crunchiness is maintained to the end due to an effect of the soybean puff that is less likely to be melted even in the latter half of the mastication.

Modification

Figure 17:
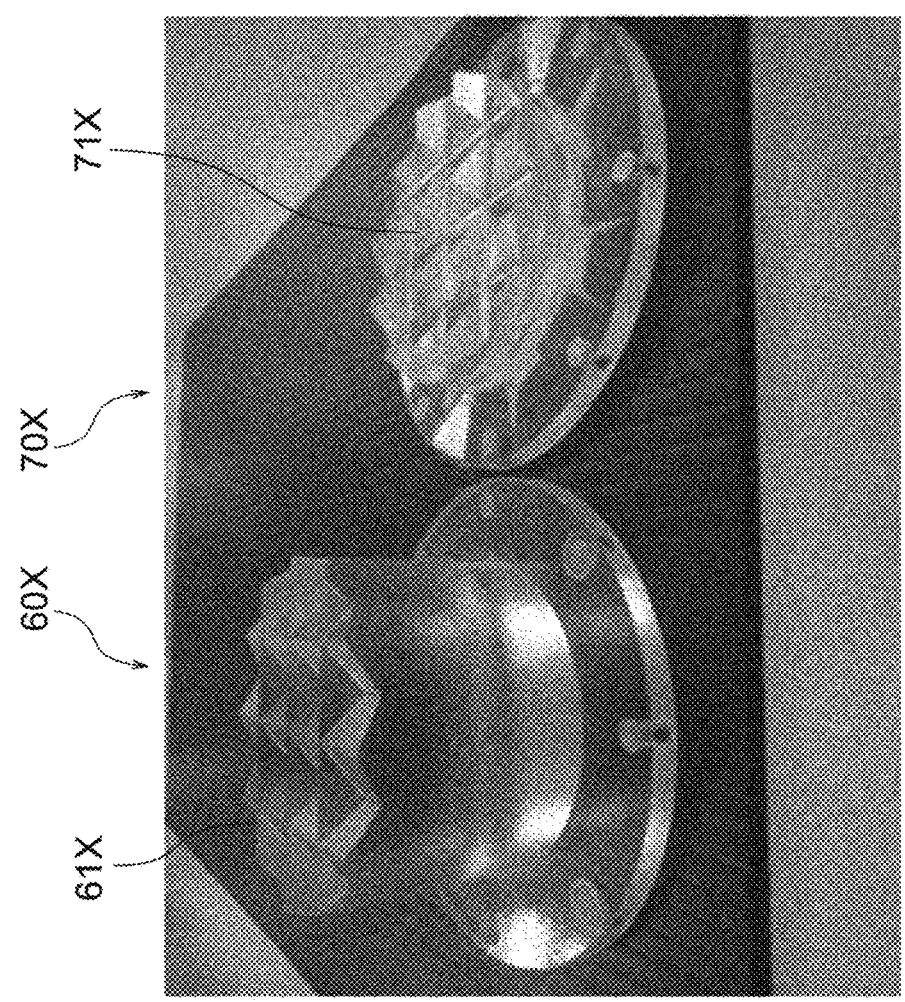
FIG. 17 is a photograph showing an upper plunger and a lower plunger of a food physical property evaluation device according to a modification.

FIG. 17 is a photograph showing an upper plunger 60X and a lower plunger 70X of a food physical property evaluation device according to a modification. A food suitable for evaluation executed by the food physical property evaluation device according to the modification is a gummy. The lower plunger 70X is provided with a lower occlusal part 71X having a shape in which a plurality of quadrangular pyramid-shaped convex portions are arranged side by side. The convex portions of the lower occlusal part 71X each have a quadrangular pyramid shape whose bottom surface is square with a side of 13 mm. The upper plunger 60X is provided with an upper occlusal part 61X having a concave-convex shape that is occluded with the plurality of convex portions of the lower occlusal part 71X.

A food physical property evaluation method using the food physical property evaluation device according to the modification will be described. A gummy, which is a food to be evaluated, is placed on the lower occlusal part 71X of the lower plunger 70X, and the lower plunger 70X is elevated to occlude the lower occlusal part 71X of the lower plunger 70X with the upper occlusal part 61X of the upper plunger 60X. At this time, the upper plunger 60X and the lower plunger 70X are occluded with each other at positions where the upper plunger 60X and the lower plunger 70X are not in contact with each other even when the upper plunger 60X and the lower plunger 70X are closest to each other. When the lower occlusal part 71X of the lower plunger 70X occludes with the upper occlusal part 61X of the upper plunger 60X, the gummy is pressed into a gap between the lower occlusal part 71X and the upper occlusal part 61X with a predetermined force. Next, the lower plunger 70X is lowered, and the occlusion of the lower occlusal part 71X of the lower plunger 70X and the upper occlusal part 61X of the upper plunger 60X is released. After the occlusion is released, the upper plunger 60X is rotated in a horizontal direction by 90 degrees until the upper plunger 60X and the lower plunger 70X reach positions where the upper plunger 60X and the lower plunger 70X are not in contact with each other even when the upper plunger 60X and the lower plunger 70X are closest to each other. By repeating the above steps, the compression is performed a plurality of times. The 90-degree rotation in the horizontal direction of the upper plunger 60X performed for each compression is reversed, for example, every two times of the compression. Except for the above configurations and operations, other descriptions are the same as in the second embodiment.

Fifth Example

In the food physical property evaluation device in the modification of the second embodiment, a test the same as that in the third example was performed on one gummy of each of four types of commercially available gummy samples (a gummy GA, a gummy GB, a gummy GC, and a gummy GD). The treatment was performed with a compression frequency of 1 time/second, a compression force of 400 N, and a number of compression of 90 times. A temperature of a plunger surface in contact with the gummy was adjusted to 32.4° C.±1.5° C. In order to simulate saliva retained in the oral cavity, 1 ml of artificial saliva was added in a device at the start, and was added at a flow rate of 4 ml/min during the test. During the test, a force applied to the upper plunger 60X by the sensor 62 was measured. From the start of the test until a two-point moving average of peak positions of the forces among outputs of the force was less than 320 N, impulses were calculated based on the outputs of the force, and a sum of the obtained impulses was calculated. The test was performed five times for each gummy, and an average value of values excluding a maximum value and a minimum value was obtained. An average value of the gummy GA was set to 5, and relative values with respect to the gummy GA were calculated for average values of the other gummies (the gummy GB, the gummy GC, and the gummy GD).

Each of the four types of commercially available gummy samples described above (the gummy GA, the gummy GB, the gummy GC, and the gummy GD) was subjected to an intake test by ten subjects, and a total masseter muscle activity during intake of the gummy was determined. Ten subjects who were determined as being appropriate for the intake test in consideration of the oral environment and the like were selected from candidates who wished to perform the intake test. During the intake test, using a physiological evaluation device described in a patent literature (JP2012-139442A), a muscle electrode was attached to the subject, and an electromyography of left and right masseter muscles from the start of mastication to swallowing of one gummy was acquired to determine the total masseter muscle activity. After the gummy was masticated and swallowed, water was drunk to remain no residue in the mouth, and the test was performed three times for each gummy to determine an average value. An average value of the gummy GA was set to 5, and relative values with respect to the gummy GA were calculated for average values of the other gummies (the gummy GB, the gummy GC, and the gummy GD).

Figure 18:
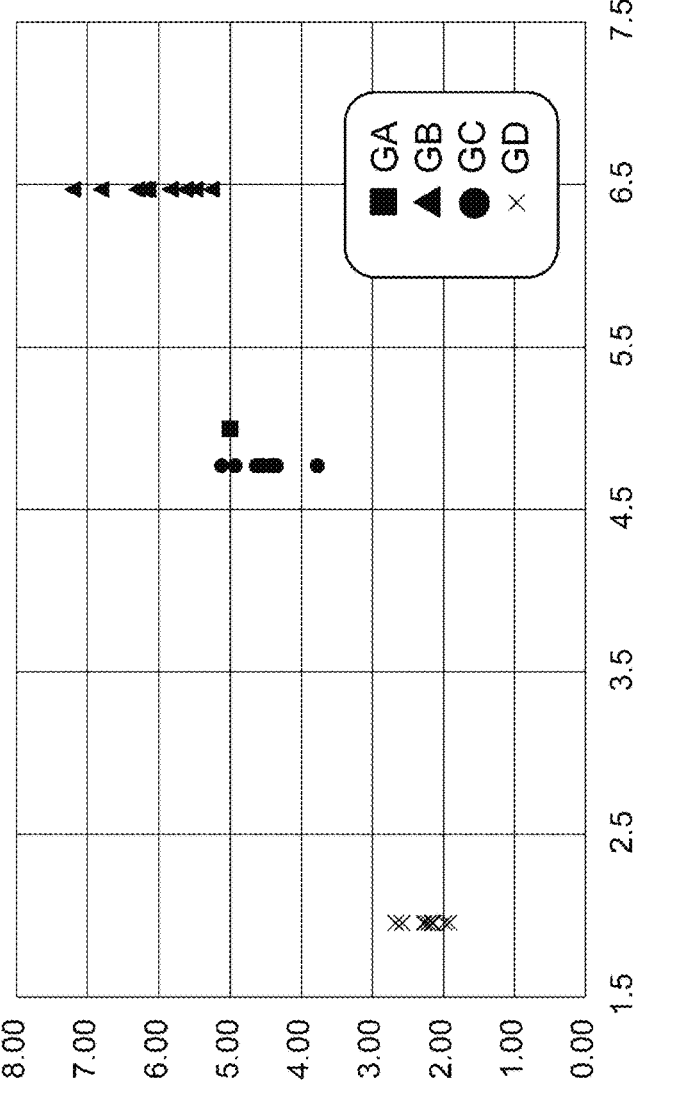
FIG. 18 is a graph showing a total masseter muscle activity (a relative value) with respect to a sum of impulses (a relative value) according to a fifth example.

FIG. 18 is a graph showing the total masseter muscle activity (a relative value) with respect to the sum of the impulses (a relative value) obtained for the gummy GA, the gummy GB, the gummy GC, and the gummy GD. It was confirmed that the sum of the impulses (the relative value) and the total masseter muscle activity (the relative value) have a strong positive correlation with a correlation coefficient of 0.97.

Figure 19:
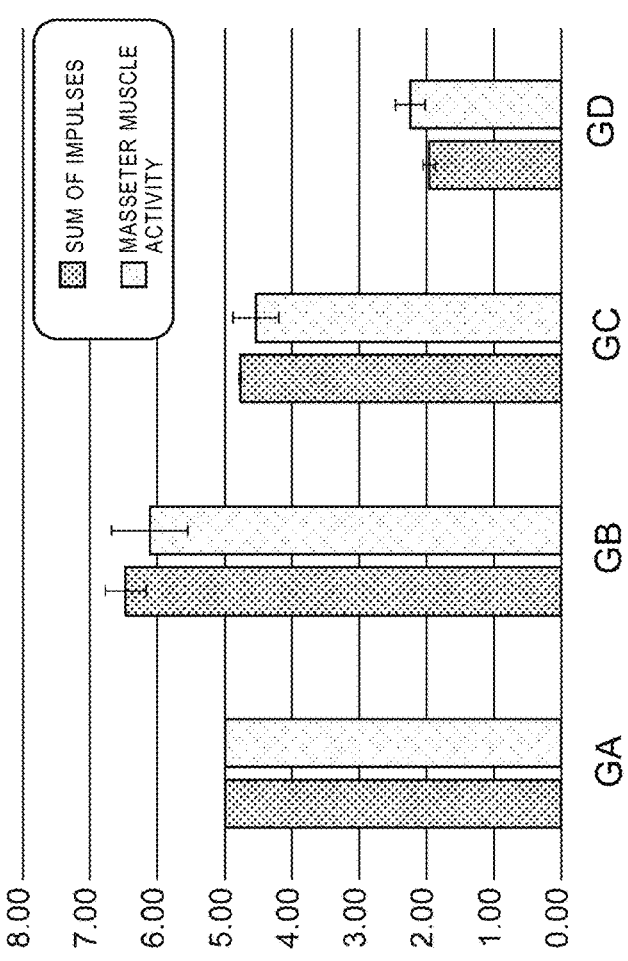
FIG. 19 is a graph showing the sum of the impulses and the total masseter muscle activity (a relative value) according to the fifth example.

FIG. 19 is a graph showing the sum of impulses and the total masseter muscle activity (relative values) obtained for the gummy GA, the gummy GB, the gummy GC, and the gummy GD. It was confirmed that the relative value of the masseter muscle activity obtained from the intake test and the relative value of the sum of impulses obtained from the food physical property evaluation device according to the second embodiment are correlated regardless of hardness and type of the gummy, and that the food physical property evaluation device according to the modification of the second embodiment has validity as a device that simulates a mastication process.

In the embodiments and the modification described above, various modifications can be made as follows without departing from the gist of the invention.

In the above embodiments, the lower plunger performs the reciprocating linear movement, and the upper plunger performs the reciprocating rotation movement, and the invention is not limited to the configuration. Configuration where at least one of the lower plunger and the upper plunger may perform the reciprocating linear movement, and at least one of the upper plunger and the lower plunger may perform the reciprocating rotation movement, may be applicable. The sensor may be incorporated in both the upper plunger and the lower plunger. The above embodiments can be applied to a device and a method of evaluating physical properties of a food other than a chocolate or a chocolate snack. A physical quantity measured by the sensor is not limited to a force (an impulse obtained by integrating from a force) and a torque, and can be applied to various physical quantities that can be detected by the upper plunger.

REFERENCE SIGN LIST

1: food physical property evaluation device
10, 60, 60X: upper plunger
11, 61, 61X: upper occlusal part
12, 62: sensor
20, 70, 70X: lower plunger
21, 71, 71X: lower occlusal part
22, 72: protective part
30: drive unit
40: measurement control unit
50: artificial saliva supply unit
51: inflow tube
61A: first convex portion
61B: second convex portion
AX: rotation axis
FA, FB: food
LR: reciprocating linear movement
RR: reciprocating rotation movement

The invention claimed is:

1. A food physical property evaluation method comprising:

placing a food to be evaluated on a lower occlusal part of a lower plunger which has a shape to occlude with an upper occlusal part of an upper plunger and faces the upper occlusal part of the upper plunger;

causing at least one of the upper plunger or the lower plunger to perform a reciprocating linear movement in a linear direction in which the upper plunger and the lower plunger are occluded and separated, causing at least one of the upper plunger or the lower plunger to perform a reciprocating rotation movement in a rotation direction with the linear direction as a rotation axis, and adjusting a pressure applied between the upper plunger and the lower plunger by a power of a motor or an elastic force of a solid elastic body; and measuring a physical quantity including: (i) a force applied to the upper plunger or the lower plunger; and (ii) a torque applied to the upper plunger or the lower plunger, and evaluating food physical properties based on the physical quantity.

2. The food physical property evaluation method according to claim 1, wherein;

the force applied to the upper plunger or the lower plunger is measured; and the food physical properties are evaluated based on a value of the force applied to the upper plunger or the lower plunger.

3. The food physical property evaluation method according to claim 1, wherein:

the force applied to the upper plunger or the lower plunger is measured, and an impulse is calculated based on the force applied to the upper plunger or the lower plunger; and the food physical properties are evaluated based on a value of the impulse.

4. The food physical property evaluation method according to claim 1, wherein;

the torque applied to the upper plunger is measured; and the food physical properties are evaluated based on a value of the torque applied to the upper plunger or the lower plunger.

5. The food physical property evaluation method according to claim 1, further comprising obtaining a profile of a temporal change in the physical quantity, wherein the food physical properties are evaluated based on the profile of the temporal change in the physical quantity.

6. The food physical property evaluation method according to claim 1, wherein:

the force applied to the upper plunger or the lower plunger is measured; and the food physical property evaluation method further comprises obtaining a profile of a temporal change in the force applied to the upper plunger or the lower plunger, and the food physical properties are evaluated based on the profile of the temporal change in the force applied to the upper plunger or the lower plunger.

7. The food physical property evaluation method according to claim 1, wherein:

the force applied to the upper plunger or the lower plunger is measured, and an impulse is calculated based on the force applied to the upper plunger or the lower plunger; and the food physical property evaluation method further comprises obtaining a profile of a temporal change in the impulse, and the food physical properties are evaluated based on the profile of the temporal change in the impulse.

8. The food physical property evaluation method according to claim 1, wherein;

the torque applied to the upper plunger or the lower plunger is measured; and the food physical property evaluation method further comprises obtaining a profile of a temporal change in the torque applied to the upper plunger or the lower plunger, and the food physical properties are evaluated based on the profile of the temporal change in the torque applied to the upper plunger or the lower plunger.

\* \* \* \* \*